(12) United States Patent
Handyside

(10) Patent No.: US 11,111,540 B2
(45) Date of Patent: Sep. 7, 2021

(54) ASSESSMENT OF RISK OF ANEUPLOIDY

(71) Applicant: BLUEGNOME LTD, Cambridgeshire (GB)

(72) Inventor: Alan Handyside, Sussex (GB)

(73) Assignee: BLUEGNOME LTD, Cambridgeshire (GB)

( * ) Notice: Subject to any disclaimer, the term of this patent is extended or adjusted under 35 U.S.C. 154(b) by 96 days.

(21) Appl. No.: 15/905,665

(22) Filed: Feb. 26, 2018

(65) Prior Publication Data
US 2018/0291454 A1 Oct. 11, 2018

Related U.S. Application Data

(63) Continuation of application No. 14/760,630, filed as application No. PCT/GB2014/050955 on Mar. 26, 2014, now Pat. No. 9,944,987.

(30) Foreign Application Priority Data

Mar. 27, 2013 (GB) ..................................... 1305588
Jan. 10, 2014 (GB) ..................................... 1400397

(51) Int. Cl.
*C12Q 1/6883* (2018.01)
*C12Q 1/6827* (2018.01)
*G16B 20/20* (2019.01)

(52) U.S. Cl.
CPC ......... *C12Q 1/6883* (2013.01); *C12Q 1/6827* (2013.01); *G16B 20/20* (2019.02); *C12Q 2539/115* (2013.01); *C12Q 2600/156* (2013.01)

(58) Field of Classification Search
None
See application file for complete search history.

(56) References Cited

U.S. PATENT DOCUMENTS

2006/0134674 A1* 6/2006 Huang ................. C12Q 1/6827
435/6.12
2008/0166715 A1 7/2008 Hillis
2010/0160717 A1 6/2010 Scott et al.
2010/0185176 A1 7/2010 Vinten-Johansen

FOREIGN PATENT DOCUMENTS

WO 2005032341 4/2005
WO 2006055761 5/2006
WO WO-2011146632 A1 * 11/2011 ........... C12Q 1/6883

OTHER PUBLICATIONS

Gabriel et al Chromosome Res. 2011. 19: 155-163.*
Altarescu, et al., "Gene location matters: polar body analysis has limited informativity in centromeric genes", Reproductive BioMedicine Online, vol. 18, Supplement 3, 2009, S-10-S-11.
Christopikou, et al., "Polar body analysis by array comparative genomic hybridization accurately predicts aneuploidies of maternal meiotic origin in cleavage stage embryos of women of advanced maternal age", Human Reprod vol. 28, No. 5, Mar. 10, 2013, 1426-1434.
Gabriel, et al., "Array comparative genomic hybridisation on first polar bodies suggests that non-disjunction is not the predominant mechanism leading to aneuploidy in humans", J Med Genet vol. 48, May 26, 2011, 433-437.
Gomes, et al., "Preconceptional diagnosis for Robertsonian translocation as an alternative to preimplantation genetic diagnosis in two situations: a pilot study", J Assist Reprod Genet vol. 26, Jan. 29, 2009, 113-117.
Gutierrez-Mateo, et al., "Karyotyping of human oocytes by cenM-FISH, a new 24-colour centromere-specific technique", Hum Reprod vol. 20, No. 12, Aug. 26, 2005, 3395-3401.
Handyside, et al., "Karyomapping: a universal method for genome wide analysis of genetic disease based on mapping crossovers between parental haplotypes", J Med Genet, 47, 2010, 651-658.
Handyside, et al., "Molecular origin of female meiotic aneuploidies", Biochimica et Biophysica Acta (BBA)—Molecular Basis of Disease, vol. 1822, Issue 12, Dec. 2012, 1913-1920.
Handyside, et al., "Multiple meiotic errors caused by predivision of chromatids in women of advanced maternal age undergoing in vitro fertilisation", European Journal of Human Genetics, 20, 2012, 742-747.
Chowdhury, R et al., "Genetic analysis of variation in human meiotic recombination", PLoS Genet 5, e1000648, doi:10.1371/journal.pgen.1000648, 2009.
Handyside, A. et al., "Multiple meiotic errors caused by predivision of chromatids in women of advanced maternal age undergoing in vitro fertilization", European Journal of Human Genetics (2012) 20, 742-747.
Hassold, A H. et al., "Multiple meiotic errors caused by predivision of chromatids in women of advanced maternal age undergoing in vitro fertilisation", Eur J Hum Genet 70, 2012, 742-747.
Kong, A et al., "Sequence variants in the RNF212 gene associate with genome-wide recombination rate", Science 319, doi:10.1126/science.1152422, 2008, 1398-1401.
Nagaoka, S I. et al., "Human aneuploidy: mechanisms and new insights into an age-old problem", Nat Rev Genet 13, doi:10.1038/nrg3245, 2012, 493-504.
Spandorfer, S D. et al., "Relationship between maternal age and aneuploidy in in vitro fertilization pregnancy loss", Fertil Steril 81, 2004, 1265-1269.

* cited by examiner

*Primary Examiner* — Carla J Myers

(74) *Attorney, Agent, or Firm* — Illumina, Inc.; Brent C. Moore

(57) ABSTRACT

The present disclosure relates generally to methods and materials for use in detecting abnormalities of the number of whole chromosomes or chromosome regions (aneuploidy). It has particular utility for assessing the risk of aneuploidy of eggs (i.e., oocytes), fertilised eggs or embryos developed therefrom in the context of in vitro fertilisation.

18 Claims, 9 Drawing Sheets

Figure 1:
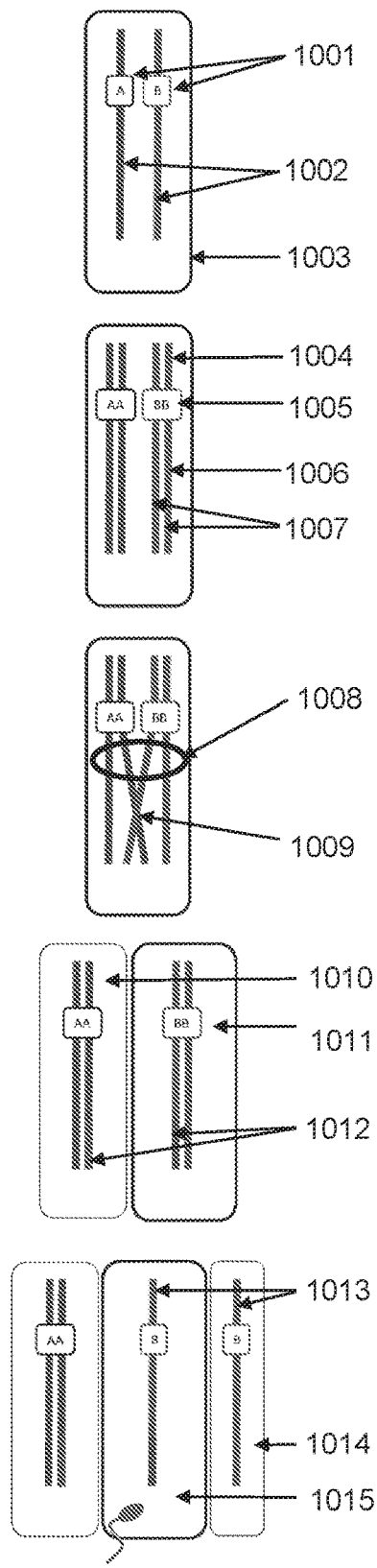

Flow chart of process for predicting aneuploidy of maternal meiotic origin in human eggs and embryos following fertilisation by analysis of centromeric heterozygosity (CH) for each chromosome

Figure 9

| Embryo # | PB1 heterozygosity pattern | Incidence | | | Embryo karyotype |
|---|---|---|---|---|---|
| | | 1 | 2 | ≥3 | |
| 2 | CH<br>Hetero<br>Homo<br>Loss | | | | Euploid |
| 7 | CH<br>Hetero<br>Homo<br>Loss | ▬▬▬<br>▬▬ | | | +22 |
| 8 | CH<br>Hetero<br>Homo<br>Loss | ▬▬ | | | +9 |
| 10 | CH<br>Hetero<br>Homo<br>Loss | ▬▬▬▬<br>▬▬ | | | +15 |
| 11 | CH<br>Hetero<br>Homo<br>Loss | ▬▬<br>▬▬ | | | +22 |
| 12 | CH<br>Hetero<br>Homo<br>Loss | | | | Euploid |
| 13 | CH<br>Hetero<br>Homo<br>Loss | ▬▬<br>▬▬▬ | | | -22 |
| 14 | CH<br>Hetero<br>Homo<br>Loss | ▬▬<br>▬▬▬ | | | -19 |
| 16 | CH<br>Hetero<br>Homo<br>Loss | ▬▬ | | | -21 |

ASSESSMENT OF RISK OF ANEUPLOIDY

CROSS-REFERENCE TO RELATED APPLICATIONS

This application is a continuation of, and claims benefits and priorities to, U.S. patent application Ser. No. 14/760,630, filed on Jul. 13, 2015, which is a national stage entry of International Application No. PCT/GB2014/050955, filed on Mar. 26, 2014, which further claims benefits and priorities to United Kingdom Application No. GB1400397.4, filed on Jan. 10, 2014 and United Kingdom Application No. GB1305588.4, filed on Mar. 27, 2013, the disclosures of which are incorporated herein by reference in their entireties.

TECHNICAL FIELD

The present disclosure relates generally to methods and materials for use in detecting abnormalities of the number of whole chromosomes or chromosome regions (aneuploidy). It has particular utility for assessing the risk of aneuploidy of eggs (i.e., oocytes), fertilised eggs or embryos developed therefrom in the context of in vitro fertilisation.

BACKGROUND ART

In normal female meiosis the precursor cells of the ova multiply and then reduce the number of chromosomes to one half set in each gamete in two specialised meiotic divisions.

Meiosis is initiated in the fetal ovary before birth during the early development of the female germ cells (primary oocytes), which will eventually form mature eggs (or oocytes, the terms are used interchangeably) in the adult female.

To reduce the number of chromosomes from the normal (euploid) 23 pairs of homologouschromosomes (one of each pair inherited from the father and one from the mother, so 46 in total) to 23 single chromosomes, there is one round of DNA replication in which each chromosome is duplicated into two sister chromatids followed by two specialised meiotic divisions, meiosis I and II.

Following replication, the two homologous chromosomes of each pair 'pair up' and a single bivalent chromosome forms in which all four sister chromatids are tightly bound together. This allows a limited number of breaks in the DNA strands of adjacent non-sister chromatids to 'crossover' and re-join the other chromatid, leading to non-recombinant (no exchange) and recombinant chromatids and generating genetic variation.

As the cell divides at the end of meiosis I, one homologous chromosome of each pair is pulled into the first polar body and the other into the secondary oocyte, which therefore now has 23 chromosomes each with two sister chromatids.

In meiosis II, following fertilisation of the oocyte by a sperm cell containing the paternal half set of chromosomes, the two sister chromatids of each chromosome finally separate and segregate into the second polar body and the fertilised oocyte (now a zygote). The zygote therefore inherits 23 single maternal chromatids (now 'chromosomes').

Aneuploidy is defined as an abnormal number of whole chromosomes or parts of chromosomes causing a genetic imbalance. The most frequent and clinically significant aneuploidies involve single chromosomes (strictly 'aneusomy') in which there are either three ('trisomy') or only one ('monosomy') instead of the normal pair of chromosomes per somatic cell.

Chromosome aneuploidy is a major cause of pregnancy loss and abnormal pregnancy with live births and increases exponentially with maternal age in the decade preceding menopause (Hassold and Hunt, 2001). Most autosomal aneuploidies and all autosomal monosomies are lethal, only a small number of trisomies are compatible with full term development often with severe congenital abnormalities.

A similar pattern of aneuploidy occurs in pregnancies following assisted conception using in vitro fertilisation (IVF) (Spandorfer et al., 2004). Furthermore, microarray based comparative genomic hybridisation (e.g., array CGH) analysis has shown that a majority of human oocytes in women of advanced maternal age (average age 40) are aneuploid, most with multiple aneuploidies (Handyside et al., 2012).

Currently, human oocytes can be tested for aneuploidy using whole genome amplification (WGA) of both the first and second polar bodies (PB1 and PB2, respectively) by microarray based comparative genomic hybridisation (array CGH). Array CGH is a methodology, which compares the amount of DNA hybridising to DNA probes spaced typically at 1 Mb intervals across the genome, i.e. across each chromosome, in test and control DNA labelled with green and red fluorochromes (24Sure™, BlueGnome Ltd; www.24Suretest.com), for example. With human oocytes, WGA products from the two polar bodies are labelled and hybridised and the signal intensities compared to control male and female DNA labelled in opposite fluorochromes.

The polar bodies are by-products of the two meiotic divisions, meiosis I and II, and since they do not form part of the embryo they can be removed with minimal effect using published methods well known to those skilled in the art. However, biopsying both polar bodies from each oocyte is labour intensive for clinics and multiple arrays are required to test each oocyte.

Other methods for detecting aneuploidy have been proposed as described herein.

For example, the presence or absence of each chromosome in polar bodies can be detected by multiplex PCR of panels of chromosome specific sequences (Advalytix, Beckman Coulter; www.advalytix.com/advalytix/). However amplification bias makes it difficult to accurately quantify the products, thereby limiting possible application for aneuploidy testing in polar bodies.

Limiting dilution into separate wells and digital PCR can be used to count the number of chromatids. However by virtue of the steps involved, this methodology can be technically challenging, and has not yet been extensively validated (for example, see publication WO2011/138750 of the MRC et al).

Thus it can be seen that novel, less complex, methods for assessing the risk of aneuploidy of eggs, fertilised eggs or embryos developed therefrom would provide a contribution to the art.

DISCLOSURE OF THE INVENTION

This disclosure provides a novel approach to assessing whether eggs (and thus fertilised eggs or embryos developed therefrom) are at increased risk of aneuploidy of maternal meiotic origin, by analysing the first polar body (PB1), optionally with other measures as described below.

Centromeric Heterozygosity (CH) in PB1 for Use in Assessing Risk

More specifically, it has been determined that an increased risk of errors in meiosis II, which would lead to aneuploidy in the fertilised egg, can be assessed by measuring total heterozygosity or centromeric heterozygosity (CH) in PB1 only, optionally with other measures as described below. In particular, where CH is present or elevated, and even where the secondary oocyte appears euploid (having 2n sister chromatids) there is an increased risk of aneuploidy following segregation in meiosis II, compared to where CH is not detected, or is at a low level.

As explained herein, the normal situation for PB1 is that it contains a chromosome consisting of predominantly or entirely homozygous sister chromatids replicated from one of the homologous chromosomes from the mother. In such a situation CH would be very low or absent.

Using CH this normal situation can be distinguished in PB1 from the abnormal presence of one or more chromosomes which comprise two or more non-sister chromatids, the chromatids being derived from both of the homologous maternal chromosomes. Such non-sister chromatids can be heterozygous at various loci, and importantly may display at least some level of CH.

Because significant CH would not arise merely from recombination, a novel system has been developed in which its presence can be used to infer a risk of aneuploidies of various types, being manifest after meiosis II.

The novel systems described herein may be employed to estimate ploidy (euploid, aneuploidy) status of the egg (and fertilised egg, and embryo).

It will be appreciated from the disclosure herein that embodiments of the disclosure are directed at assessing risk. Thus a proportion of chromosomes in which CH is present or elevated in PB1 may not result in aneuploidies, because the pattern of segregation in meiosis II nevertheless results in a euploid egg. However, the invention nevertheless has significant utility in practice because it is known that many oocytes (and resulting fertilised eggs and embryos) will have multiple aneuploidies. The present disclosure provides a clinically useful methodology for grading or selecting eggs or embryos before or after fertilisation based on relative risk.

In particular, where there is a panel of PB1s being assessed corresponding to a panel of oocytes, the disclosure herein provides a methodology based on CH for selecting one or more oocytes in which the likelihood of errors having occurred during meiosis I is reduced compared to the other oocytes. This is discussed in more detail below.

Number of Crossovers in PB1 for Use in Assessing Risk

Furthermore, parallel analysis of oocytes and PB1 by the present inventors has revealed that the total number of crossovers in the first polar body (of all the chromosomes assessed) can be correlated with a general tendency to aneuploidy.

More specifically total crossovers in some or preferably all of the chromosomes in PB1 can be estimated from the number and position of blocks of heterozygosity, and this can be used as a proxy for the total number of recombination events (crossovers, meiotic exchanges; the terms are used synonymously unless context demands otherwise) in the respective oocyte.

It is known in the art that a low frequency of recombination is associated with abnormalities in chromosome segregation and, in particular, increased levels of non-disjunction, leading to aneuploidy (see Hassold, 2001).

Therefore a relatively low number of crossovers in the first polar body can be indicative of tendency to aneuploidy of the oocyte.

For example, the detection of less than or equal to 50 recombination events across all chromosomes in PB1 may be taken to indicate a significantly higher risk in the corresponding oocyte than where average, or above average numbers (>75) are detected. The detection of equal to or between 51 and 74 events across all chromosomes in PB1 may be taken to indicate an above average risk. The detection of greater than or equal to 75 would be deemed average risk (i.e. no adverse inference to be drawn, based purely on total number of recombination events).

Location of Crossovers in PB1 for Use in Assessing Risk

It is known that chromosomes with a single proximally (close to centromere) or distally located recombination are more likely to non-disjoin than were those with more medially positioned recombinations (see Hassold, 2001). Accordingly where such a single recombination event is detected in PB1, this may also suggest a general tendency to aneuploidy in relation to that chromosome.

Other Utilities of High Resolution SNP Mapping of PB1

As shown in the Examples below, high resolution SNP mapping of PB1 can reveal de novo structural chromosome abnormalities. In particular, the inventors have shown that chromosomal structural defects in the oocyte were reflected in PB1.

Therefore in addition to CH, analysis of the number of crossovers in some or all of the chromosomes of PB1, as well as the location of crossovers, provides an alternative, or additional, methodology for assessing risks of aneuploidy. As described herein, that has utility (inter alia) in oocyte or embryo selection and/or as a diagnostic or prognostic indicator of the likelihood of successful pregnancy.

PREFERRED EMBODIMENTS

In preferred embodiments a method of assessing heterozygosity or CH is carried out by whole genome amplification (WGA) and genotyping for heterozygous loci (e.g., such as single nucleotide polymorphisms, SNPs), which for CH must be close to and flanking the centromeres of each chromosome in PB1.

Where whole genome amplification and SNP genotype analysis is performed, it may also be desirable to phase the SNPs of the maternal chromosomes. This permits the existence of heterozygosity around the centromere in PB1 to be inferred even in the event of random allele dropout at the heterozygous maternal loci, again distinguishing the 'normal situation' from the abnormal presence of two or more non-sister chromatids. As noted above, it will generally be preferred to perform SNP genotype or haplotype analysis across the entire genome, in order to assess the number and\or location of recombination sites.

Whole genome amplification and genotype analysis can additionally, optionally, be used to determine chromosomal aneuploidy resulting from meiosis I errors—for example the absence of any centromeric DNA for a given chromosome would also identify a risk of aneuploidy.

The method differs from prior art quantitative methods, such as array CGH to assess copy number change in PB1, since those methods would only identify errors in meiosis I (resulting in aneuploidy in the secondary oocyte). In the present invention potential errors and risks arising from meiosis I and II can be identified by PB1 analysis alone, reducing the time and cost. Furthermore, genotyping is in principle more reliable than quantitation because it is unaffected by amplification bias following WGA.

Some aspects and embodiments of the present invention will now be discussed in more detail:

In one aspect there is provided a method of investigating the ploidy status of a human egg (or assessing the risk of chromosomal aneuploidy of maternal meiotic origin in the egg), the method comprising assessing the heterozygosity for one or more (preferably all) the chromosomes of the first polar body of the human egg.

The data not only therefore provides information about centromeric heterozygosity (CH), but also total crossovers, and location of crossovers. These can in turn be used to infer a higher likelihood of aneuploidy—which can, for example, be inferred by a relatively low total number of cross-over events, or signature single recombination events near the centromere or telomere of a given chromosome.

In a preferred aspect there is provided a method of investigating the ploidy status of a human egg (or assessing the risk of chromosomal aneuploidy of maternal meiotic origin in the egg), the method comprising assessing the presence or degree of centromeric heterozygosity (CH) for one or more chromosomes of the first polar body of the human egg.

As explained herein, assessing the polar body can predict the risk of aneuploidy in the corresponding egg, and thus also the fertilised egg or embryo following meiosis II.

Preferably a plurality or panel or chromosomes is assessed.

Preferably a plurality of different first polar bodies is assessed, and the corresponding eggs, or fertilised eggs or embryos developed therefrom, are graded according to risk as described herein. This may in turn be used as part of a method of IVF.

In particular the presence of a higher level of centromeric heterozygosity (CH) in a first polar body can be used to infer a higher risk of said chromosomal aneuploidy in the corresponding egg or embryo developed therefrom compared to an absence or lower level of CH in a first polar body.

The assessment of risk by CH can also, additionally, utilise:
(i) total crossovers in PB1;
(ii) location of crossovers of chromosomes in PB1.

In one embodiment, methods disclosed herein are based on using CH to distinguish a 'normal' PB1 which contains a chromosome consisting of homozygous sister chromatids replicated from one of the homologous chromosomes from the mother, from an 'abnormal' PB1 wherein the chromosomes comprise two or more non-sister chromatids, collectively being derived from both of the homologous maternal chromosomes. This information, optionally with crossover number and\or location analysis, may be used to infer a risk of aneuploidies, of various types, being manifest after meiosis II.

The PB1 may be from a post-pubescent human female of any age. Optionally the PB1 may be from a human female of 35 years or older. Practically, the PB1 may be from a human subject (of any age) who may have, or is suspected of having, fertility problems or has or carries an inheritable disease. The PB1 may be from a human subject undergoing IVF treatment.

In one aspect, the present invention provides a method for in vitro fertilisation utilising a fertilised egg or embryo predicted to be at relatively low risk of aneuploidy according to results derived by practicing a method of the invention. "Relatively low risk" in this context means by comparison with other fertilised eggs or embryos for which the corresponding PB1s have also been assessed according to a method of the invention.

Unless context demands otherwise, where "a" or "the" chromosome is referred to herein in respect of SNP genotyping, this refers to typing a plurality of copies of that chromosome (or corresponding chromatid or chromatids) which are present in the target cell.

In one embodiment at least 2, 3, 4, 5 or 6 or all of the human chromosomes selected from the following group are assessed: X, 22, 21, 18, 16 and 13. Imbalances in any of these chromosomes may be associated with viable but abnormal pregnancies. A preferred combination of chromosomes for assessment comprises chromosomes 21, 18 and 13.

Preferably a total of at least 5, 10, 15 or 20 chromosomes are assessed.

In one embodiment the entire genome of PB1 is assessed (i.e. the CH of all 23 chromosomes is analysed). This is particularly desired where total crossover number in PB1 is to be assessed, in order to detect the existence of a low frequency of crossovers or recombination.

Preferably total heterozygosity and\or CH is assessed in the methods described herein by genotyping a plurality of SNP loci. These include genome sequencing e.g. by methods such as so called "Next Generation sequencing" (NGS)—see e.g. www.illumina.com.

Preferably total heterozygosity and\or CH assessment is preceded by WGA.

The assessment based on total heterozygosity and\or CH may or may not be used in conjunction with (prior to, or subsequently to) quantitation methods.

As discussed herein, SNPs can be interrogated using conventional techniques. This may be preceded by one or more conventional amplification steps.

In one embodiment the invention first comprises identifying the position of centromeres in the sequence of consecutive SNPs across each chromosome to be assessed.

The invention may thus comprise interrogating closely adjacent biallelic SNPs flanking the centromeres of the chromosomes of PB1.

In one embodiment equal to or at least 25, 30, 40, 50, 75, 100, 200, 300, 400, 500 or more SNPs flanking the centromere are interrogated. Preferably at least around 200 SNPs are assessed.

This number may be interrogated on each of the p and q arms of each chromosome (or q arms only for acrocentric chromosomes).

However for individual chromosomes a lesser number may be sufficient—this can be assessed by those skilled in the art according to the preferred method of typing and the accuracy associated with it and with any optional method of amplification employed.

In one embodiment 200 SNPs across a 2 Mb region of the chromosome within 5-10 Mb of the centromere are analysed.

Once the SNPs have been interrogated, the proportion of heterozygous ('AB') SNPs can be established.

A proportion of these interrogated SNPs within the region genotyped flanking the centromere exceeding e.g. 50, 60, 70, 80, 90, or 100% can be taken as being highly heterozygous ("high CH") in accordance with the methods described herein.

Recombination is significantly less frequent near the centromere (see Lynn, A., Ashley, T., and Hassold, T. (2004). Variation in human meiotic recombination, Annu Rev Genomics Hum Genet 5, 317-49). Thus it can be inferred that high levels of CH are associated with the presence of homologous maternal chromosomes as opposed to sister chromatids. In this respect it is highly preferable to use maternal genomic DNA as a reference when performing the methods or other aspects of the invention.

Thus it is preferable to calculate the proportion of maternal heterozygous (AB) SNPs which are also heterozygous in the first polar body. In this case equal to, or at least, 5, 10, 15, 20, 25, 50, 100, 200 or more heterozygous (in the maternal cell) SNPs per flank may be assessed.

A number of these e.g. exceeding 10, 20, 30, 40, or a proportion of these e.g. exceeding 50, 60, 70, 80, or 90% can be taken as being "highly" heterozygous in accordance with the methods described herein. It will be understood that even a minimal block (of even 5 or more, or 10 or more) of heterozygous SNPs within the centromeric region genotyped (proximal) can be indicative of high heterozygosity in accordance with the methods described herein. The presence of such heterozygous SNPs found on both sides of the centromere would provide additional, but not required, confirmation. Those skilled in the art will appreciate from the disclosure herein that the chosen threshold will be that which accommodates the small likelihood of recombination occurring close to the centromere in the region genotyped and\or any 'miscalls' or 'allele drop-ins', the likelihood of which will depend on the detection technology adopted. The present inventors have determined that background drop-ins (i.e. where a homozygous allele may be called as heterozygous) can be kept to extremely low levels, being less than 5% in the examples tested. Thus a threshold of great than 5% heterozygosity is preferred.

As explained in more detail herein, by phasing SNPs on the maternal chromosomes, any effect of random allele dropout at heterozygous maternal loci can be minimised. Thus in one embodiment the presence or a higher level of CH in a first polar body, for example as compared to a threshold proportion of heterozygous alleles in a normal first polar body, and can be correlated with an increased risk of chromosomal aneuploidy in the corresponding egg or embryo resulting from, for example, mis-segregation of single chromatids in meiosis II. As explained in the Examples this may follow bi-orientation of bivalent chromosomes in metaphase I of meiosis I. Said mis-segregation can lead to an egg lacking the relevant chromosome, or in which both homologous maternal chromosomes are present (see e.g. FIG. 4).

Figure 2:
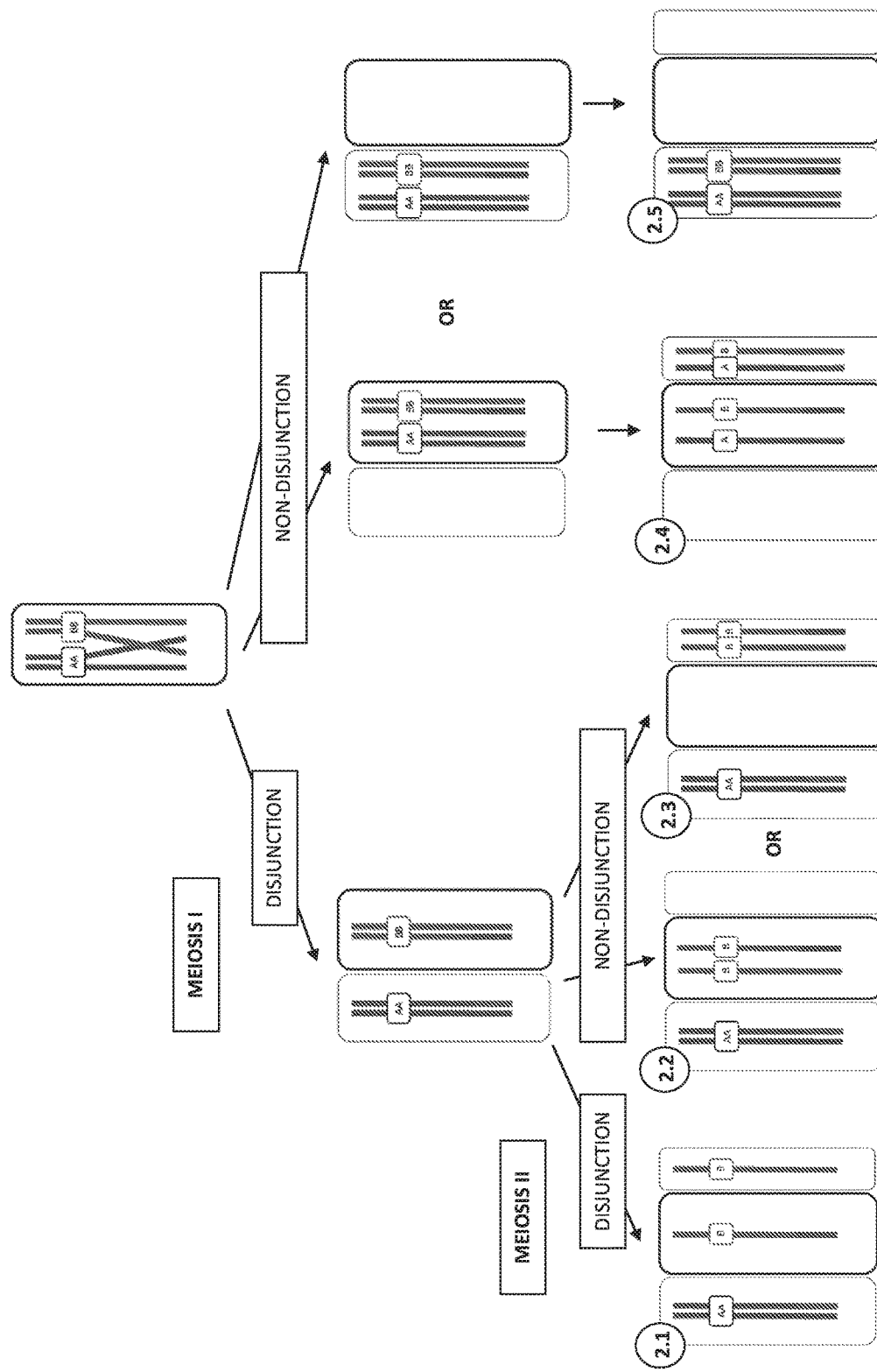

In another embodiment the presence or a higher level of CH in a first polar body may be correlated with an increased risk of chromosomal aneuploidy in the corresponding egg or embryo resulting from non-disjunction of bivalent chromosomes in meiosis I leading to an egg in which both homologous maternal chromosomes are present (see e.g. FIG. 2)

In a different embodiment a lack of centromeric alleles in a first polar body implies a higher risk of chromosomal aneuploidy in the corresponding egg or embryo developed therefrom (compared to the presence of centromeric alleles). Said absence may imply non-disjunction of bivalent chromosomes in meiosis I which leads to an egg lacking the relevant maternal chromosome (see e.g. FIG. 2).

In certain embodiments it may be desired to additionally subject the nucleic acid in PB1 to quantitation e.g. using quantitative fluorescent PCR or any other known method. This can provide, for example, more detailed information regarding the ploidy of the fertilised egg or embryo.

Figure 3:
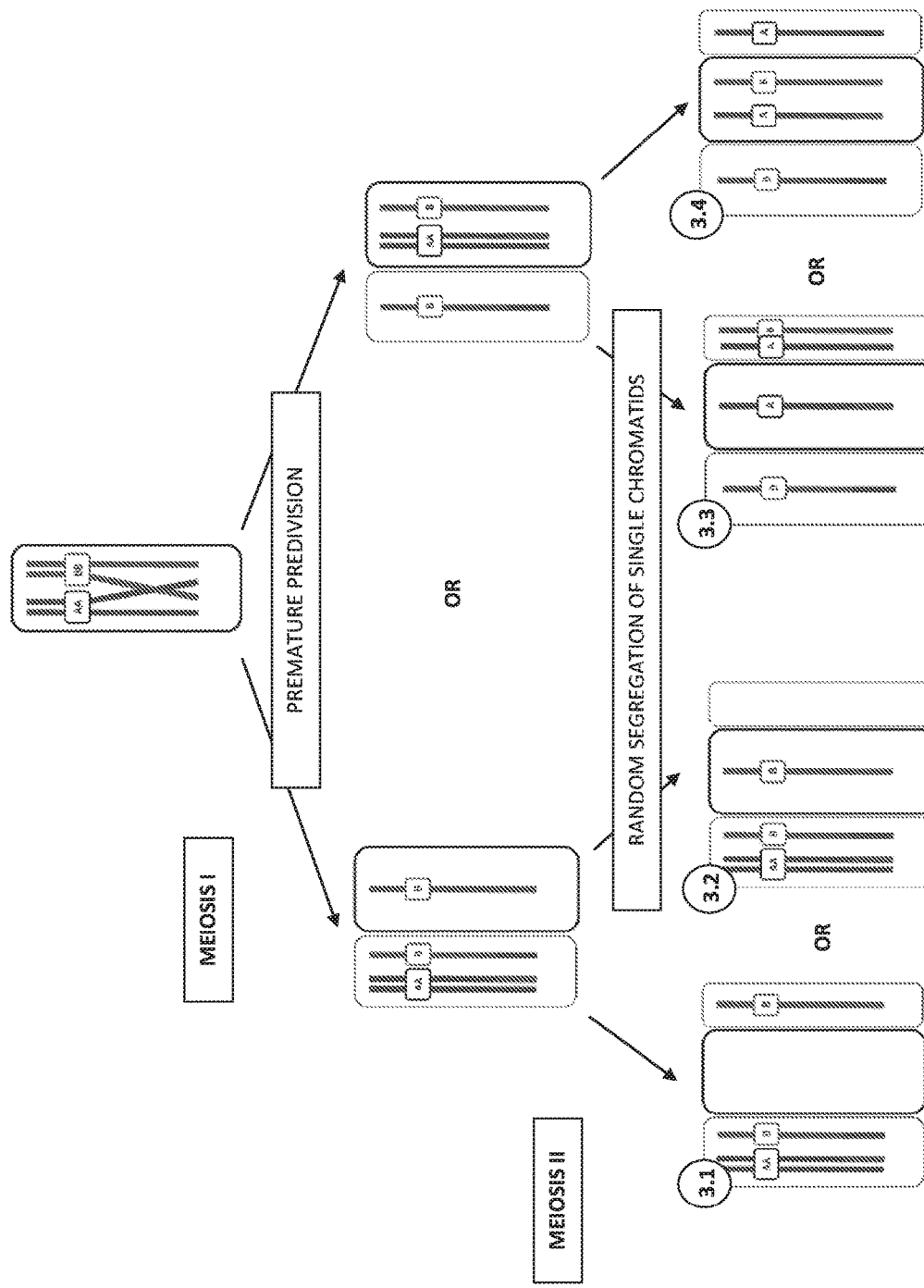
Figure 4:
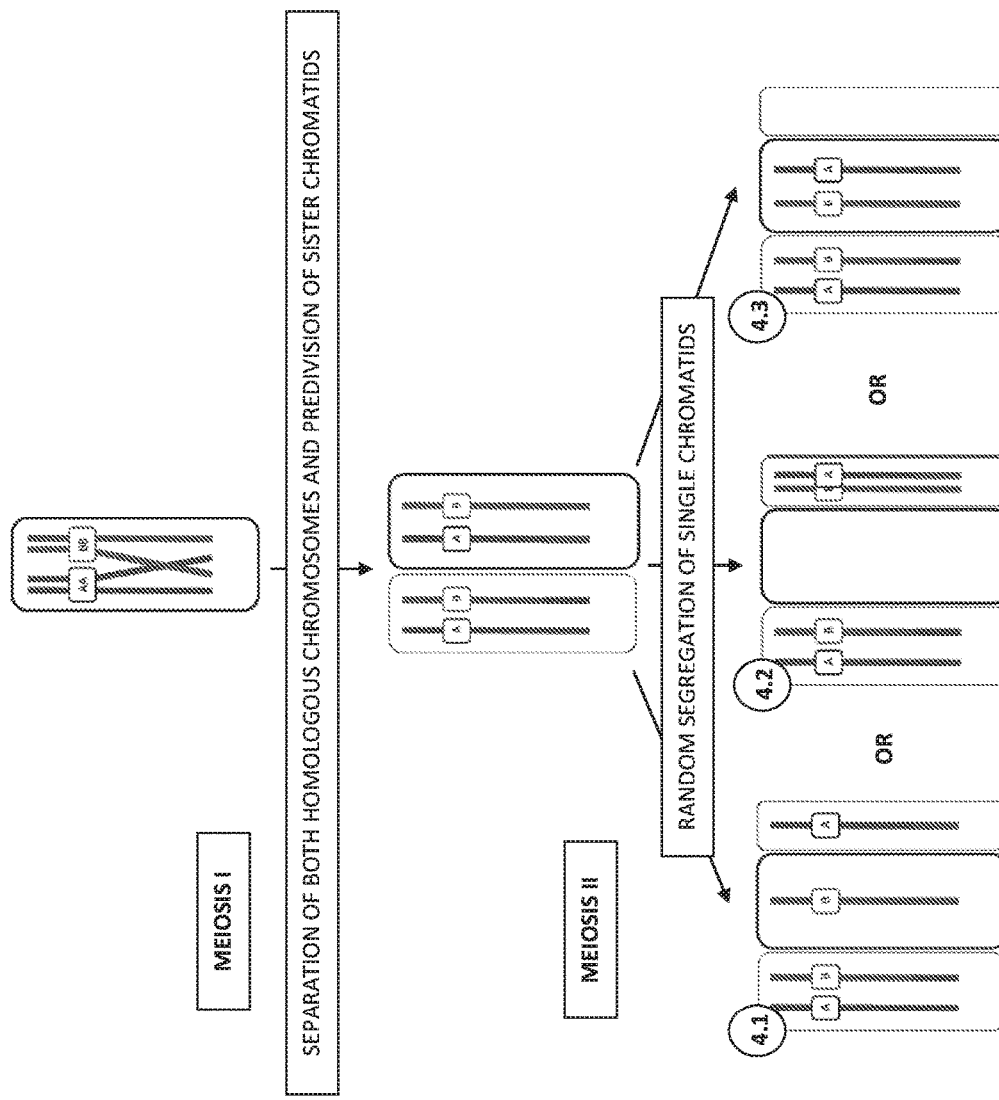
Figure 5:
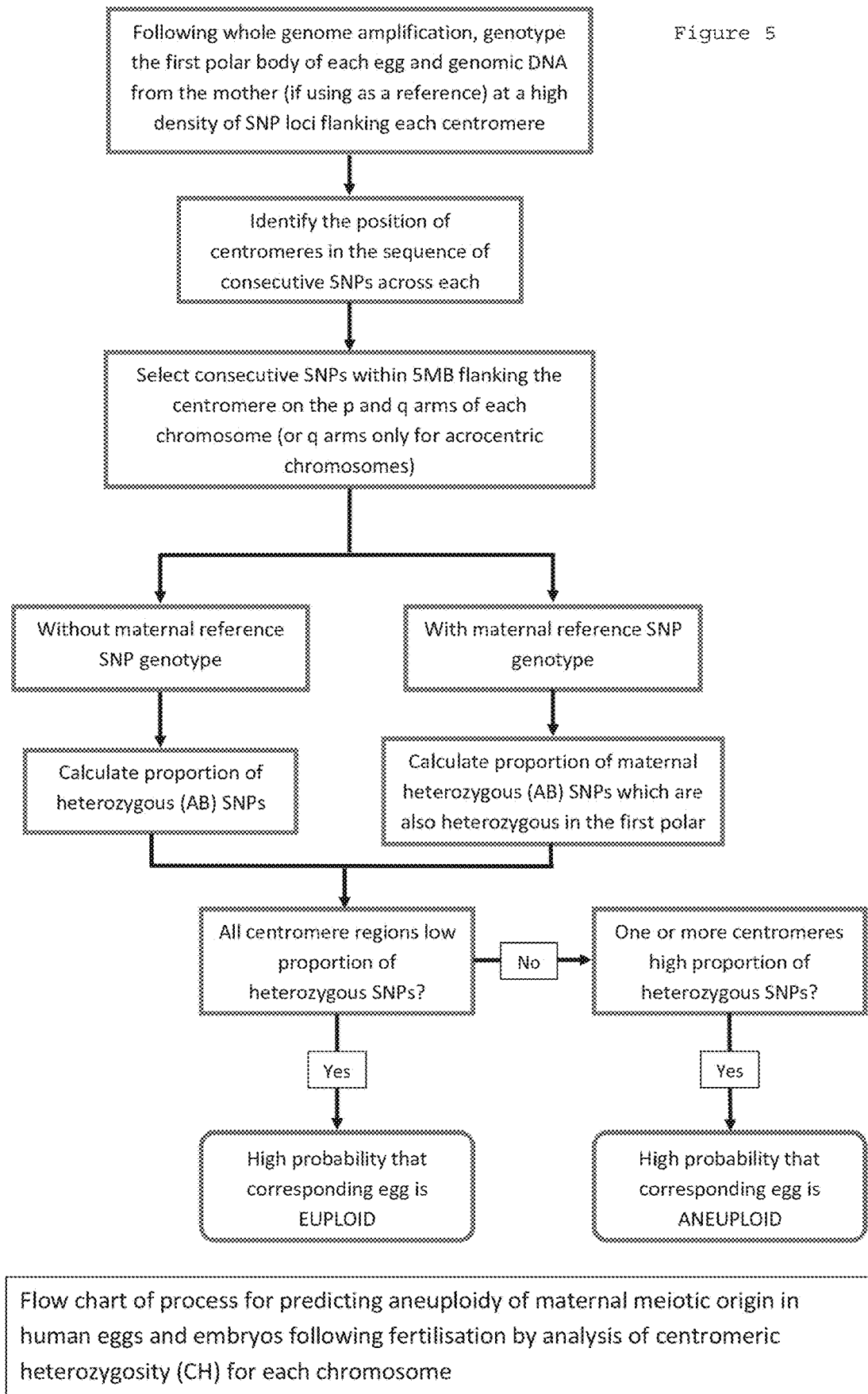

For example where the presence or a higher level of CH has been determined, and the first polar body is determined as being euploid having 2n chromatids per chromosome, the presence or a higher level of CH can imply an increased likelihood of chromosomal aneuploidy of maternal meiotic origin resulting from the 2nd meiotic division of the secondary oocyte following fertilisation (see e.g. FIG. 4).

Where an absence or lower level of CH has been determined, and the first polar body is determined as being aneuploid having 0n chromatids for one or more chromosomes, this can imply chromosomal aneuploidy of maternal meiotic origin resulting from the 1st meiotic division of the primary oocyte e.g. resulting from non-disjunction of bivalent chromosomes (see e.g. FIG. 2).

Where the presence or a higher level of CH has been determined, and the first polar body is determined as being aneuploid having 4n chromatids for one or more chromosomes, this can imply chromosomal aneuploidy of maternal meiotic origin resulting from the 1st meiotic division of the primary oocyte e.g. resulting from non-disjunction of bivalent chromosomes (see e.g. FIG. 2).

Where the presence or a higher level of CH has been determined, and the first polar body is determined as being aneuploid having 3n chromatids for one or more chromosomes, this can imply chromosomal aneuploidy of maternal meiotic origin resulting from the 1st meiotic division of the primary oocyte e.g. resulting from premature predivision of chromatids (see e.g. FIG. 3)

Where an absence or lower level of CH has been determined, and the first polar body is determined as being aneuploid having 1 n chromatids for one or more chromosomes, this can imply chromosomal aneuploidy of maternal meiotic origin resulting from the 1st meiotic division of the primary oocyte e.g. resulting from premature predivision of chromatids (see e.g. FIG. 3).

This is summarised in Table 1 below. Referring to the Table, the normal first polar body centromeric SNP genotype would be AA or BB (no CH) and the normal maternal chromosome copy number in a zygote is 1.

Any aspect or embodiment of the invention may further embrace characterising a zygote (fertilised egg, or embryo) as having either a normal segregation pattern or one of the abnormal segregation patterns as described in Table 1 by assessing the PB1 CH and optionally chromosome copy number e.g. in accordance with the combinations shown in Table 1.

Any aspect or embodiment of the invention may further embrace predicting the maternal chromosome copy number in a zygote (fertilised egg, or embryo) as being any of:

0
1
2
0 or 1
1 or 2
0, 1 or 2 by assessing the PB1 CH and preferably chromosome copy number e.g. in accordance with the combinations shown in Table 1.

TABLE 1

| Segregation pattern | FIG. reference | First polar body centromeric SNP | First polar body chromosome copy number | Maternal chromosome copy number in zygote |
|---|---|---|---|---|
| Normal | 2.1 | AA or BB | 2 | 1 |
| Non-disjunction – Meiosis II | 2.2 | AA or BB | 2 | 2 |
|  | 2.3 | AA or BB | 2 | 0 |

TABLE 1-continued

| Segregation pattern | FIG. reference | First polar body centromeric SNP | First polar body chromosome copy number | Maternal chromosome copy number in zygote |
|---|---|---|---|---|
| Non-disjunction – Meiosis I | 2.4 | No result | 0 | 2 |
| | 2.5 | AB * | 4 | 0 |
| Premature predivision – Meiosis I | 3.1 | AB * | 3 | 0 |
| | 3.2 | AB | 3 | 1 |
| | 3.3 | AA or BB | 1 | 1 |
| | 3.4 | AA or BB | 1 | 2 |
| Biorientation of chromosome – Meiosis III | 4.1 | AB | 2 | 1 |
| | 4.2 | AB * | 2 | 0 |
| | 4.3 | AB * | 2 | 2 |

Utility and Prognostic Applications

A non-limiting list of utilities for the present invention includes PB1 analysis alone as a screen to prioritise embryos for transfer and provide prognostic information to the prospective parent, and PB1 followed by PB2 for aneuploidy diagnosis and embryo selection, where increased accuracy is required.

Currently, the selection of one or more embryos, for example for transfer in IVF treatments, may be carried out on the basis of a relatively crude morphological scoring system which categorises each embryo, typically on a scale of 1-4. The score is based on the number of cells an embryo should have attained by the time of the observation, how evenly the cells of the embryo have divided, the presence of any visible nuclear abnormalities, and so on. The relevant number of embryos is then selected with either the best scores or co-equal scores.

The use of total heterozygosity and\or CH screening provides an important addition or alternative to these morphological or morphokinetic methods. As explained above, the detection of total heterozygosity and\or CH can highlight the increased possibility of aneuploidy outcomes (see e.g. scenarios 2.5, 3.1, 4.2 and\or 4.3 in Table 1, which are marked with an *). This information may thus be used to estimate a risk of aneuploidy and\or simply to select or grade eggs according to relative risk. The total heterozygosity and\or CH analysis may be done in combination with chromosome copy number. However, as is apparent from 4.2 and 4.3, this assessment can have utility even where a quantitative assessment has shown a normal copy number for the relevant PB1 or when morphological or morphokinetic analysis does not permit effective selection.

Preferably in conjunction with known relationships or correlations between populations of women of different ages and types of infertility, and optionally the other assessments described herein, the incidence of totally heterozygous and\or CH chromosomes in PB1s of their oocytes is used as a general prognostic indicator of increased risk of aneuploidy and therefore reduced chance of pregnancy. Based on the above analysis, an actual risk of aneuploidy can be estimated by inferring the likelihood of meiotic errors of the types shown in the Figures and\or by using experimental evidence in which totally heterozygous and\or CH chromosomes are followed up by copy number analysis by, for example, array CGH in the corresponding embryos, to establish actual incidence of abnormal segregation in meiosis.

More specifically, it has been demonstrated that most errors (>90%) in oocytes are caused by premature predivision of sister chromatids (FIG. 3) and very few are caused by non-disjunction of whole chromosomes (FIG. 2). If CH is identified for a particular chromosome it is therefore highly likely to be caused by premature predivision or biorientation (see Table 1 above). In the former case, a single chromatid is present in the secondary oocyte and will segregate at random to either PB2 or the fertilised oocyte on completion of the 2nd meiotic division following fertilisation. From first principles, the probability of aneuploidy (fertilised egg missing that chromosome) can be taken as 50%. Similarly for biorientation, two single chromatids are present in the secondary oocyte and these also segregate at random to either PB2 or the fertilised egg following meiosis. Thus, on this basis, the probability of both chromatids segregating to the polar body or oocyte is 25% (causing maternal monosomy and trisomy, respectively). If the probability that one chromatid segregates to PB2 and one to the fertilised egg (euploid) is 50%, a PB1 chromosome exhibiting CH has about a 50% probability of resulting in aneuploidy.

If two or more chromosomes are identified as having CH the probability that the fertilised egg is aneuploid for at least one of those chromosomes can be calculated as a standard cumulative binomial probability using the formula:

$$b(x;n,P) = nCx * Px * (1-P)n-x$$

where x: The number of successes that result from the binomial experiment.

n: The number of trials in the binomial experiment. P: The probability of success on an individual trial. 1-P: The probability of failure on an individual trial.

b(x; n, P): Binomial probability—the probability that an n-trial binomial experiment results in exactly x successes, when the probability of success on an individual trial is P.

nCr: The number of combinations of n things, taken r at a time.

Thus the probability of a fertilised egg with the following number of: chromosomes with CH having 1 aneuploidies is 1 0.5
2 0.75
3 0.875
4 0.9375
7 0.96875

More generally, where one or more centromeres display a high proportion of heterozygous alleles (e.g. SNPs) indicating one or more CH chromosomes there is a higher probability that the corresponding egg (or fertilised egg, or embryo) is aneuploid, compared to a PB1 having a lower degree of CH.

Where all centromeric regions display a low proportion of heterozygous alleles (e.g. SNPs) and it is inferred there are zero (0) CH chromosomes, there is a higher probability that the corresponding egg (or fertilised egg, or embryo) is euploid.

In practice, oocytes (which are subsequently fertilised normally) with 0 CH chromosomes can be selectively transferred ahead of those with 1, 2 or more CH-displaying chromosomes, with the aim of transferring those with an increased likelihood of having a normal number of maternal chromosomes increasing pregnancy rates and reducing miscarriage rates.

If desired, those skilled in the art can utilise morphokinetic or other morphological analysis in conjunction with the assessment of risk made using total heterozygosity and\or CH, as well as crossover number and\or location analysis.

In summary, it can be seen that where there are a number of fertilised eggs or embryos suitable for implantation, the present methods can assist in maximising the chance of selecting embryos which are euploid, and hence more likely to proceed to full term development without congenital abnormalities.

Any of the methods or systems described herein may thus further comprise the step of selecting an embryo or fertilised egg wherein PB1 exhibits CH or high CH, or in which the PB1 CH otherwise indicates the presence or likely presence of an aneuploidy in the embryo or fertilised egg.

Maternal Reference

As previously explained, the accuracy of detection of heterozygous SNPs in the regions flanking the centromeres is greatly improved by limiting the SNP analysis to those SNPs which are heterozygous in the mother and determining which of these is heterozygous in PB1. As will be readily appreciated, the mother's SNP genotype can be obtained from genomic DNA from a blood sample or discarded maternal cumulus cells which surround the egg when it is collected. Alternatively, given a number of PB1 genotypes the maternal genotype can be reconstructed on the assumption that most pairs of maternal chromosomes will segregate normally in the 1st meiotic division—for example wherever the genotype is AA in one or more PB1 and BB in others, it is likely that the maternal genotype is AB.

Phasing of Maternal Heterozygous SNPs

This can be achieved using standard genetic analysis (see e.g. Kong, 2008; Chowdhury, 2009) for example, the phasing of the two haplotypes on the two homologous chromosomes can be ascertained by genotyping the DNA of the mother and comparing the results with one or more polar bodies. Both PB1 and PB2 should normally be homozygous for one or other haplotype and by examining several of these the haplotypes can be reconstructed with a high degree of accuracy.

Thus in one embodiment SNP haplotype (and hence phasing of heterozygous SNPs) is derived from analysis of multiple single haploid gametes or PB1s.

PB2 Reference

Although the method presented herein envisages analysing centromeric SNPs (or genome-wide SNPs) in PB1 alone, and inferring the probability or relative risk of aneuploidy based on the abnormal condition of heterozygosity, it will be appreciated that analysis of both PB1 and PB2 for CH would provide confirmation of the euploid/aneuploid status of chromosomes with CH in PB1.

Analysis of SNP Loci Across the Chromosome

In one embodiment, genome wide SNP arrays are used to genotype SNP loci beyond the region flanking the centromere, thereby extending into regions where recombination is not supressed e.g. across the full length of each chromosome. Put another way, the primary analysis of SNP loci flanking each centromere, as explained in detail above, can be extended along each chromosome arm to give further information about ploidy.

In a normally segregating chromosome analysed in the PB1 following completion of meiosis I, each chromosome is homozygous (at heterozygous maternal loci) for one of the two maternal haplotypes in the region flanking the centromere. Beyond the first crossover, however, one of the two sister chromatids has a segment from the other homologous chromosome resulting in heterozygosity at all heterozygous maternal SNP loci. This pattern of alternating homozygous and heterozygous bands is repeated as further crossovers occur down each arm. This results in a characteristic pattern for each chromosome according to the typical number and location of each crossover.

Three abnormal patterns could be used to extend the CH analysis at the centromeres:

The presence of two chromatids from one homologous chromosome with a sister chromatid from the other homologue (caused by premature predivision) in PB1 will cause CH and the size of the homozygous bands further down the chromosome will be reduced or non-existent compared to the normal pattern because of a different pattern of crossovers (see FIG. 3, reference 3.1 and 3.2 compared to FIG. 4, reference 4.1, 4.2, 4.3).

The presence of both homologous chromosomes (all four sister chromatids) in PB1 will cause all maternal heterozygous SNP loci to be heterozygous along the entire length of the chromosome (see FIG. 2, reference 2.5 compared to 4.1, 4.2, 4.3).

The presence of only one sister chromatid in PB1 will result in all SNP loci being homozygous across the full length of the chromosome indicating a risk of trisomy in the corresponding oocyte following fertilisation (see FIG. 3, reference 3.3 and 3.4). It should be noted that a homologous chromosome with no crossovers will give a similar pattern but this is also abnormal and liable to result in aneuploidy.

As noted above, assessing the number and location of crossovers has more direct utility in establishing a tendency towards aneuploidy—for example if it is revealed that recombination frequency is low, or that recombination has occurred only near the centromere or telomere.

Interrogation of SNPs

Various methods for large scale single nucleotide polymorphism (SNP) analysis exist (see Syvanen, 2005, especially Table 1 therein). These include SNPstream (Bell, P. A. et al. SNPstream UHT: ultra-high throughput SNP genotyping for pharmacogenomics and drug discovery. Biotechniques Suppl., 70-72, 74, 76-77 (2002)); Genorama, APEX (Kurg, A. et al. Arrayed primer extension: solid-phase four-colour DNA resequencing and mutation detection technology. Genet. Test. 4, 1-7 (2000)); GeneChip 100K (Matsuzaki, H. et al. Genotyping over 100,000 SNPs on a pair of oligonucleotide arrays. Nat. Methods 1, 109-111 (2004)); Perlegen wafers (Hinds, D. A. et al. Whole-genome patterns of common DNA variation in three human populations. Science 307, 1072-1079 (2005)); Molecular Inversion Probes (Hardenbol, P. et al. Highly multiplexed molecular inversion probe genotyping: Over 10,000 targeted SNPs genotyped in a single tube assay. Genome Res. 15, 269-275 (2005)); GoldenGate Assay (Fan, J. B. et al. Highly parallel SNP genotyping. Cold Spring Harb. Symp. On Quant. Biol. LXVII, 69-78 (2003)). Other methods include the Illumina "BeadArray" described below. It will also be understood that genome sequencing platforms (for example as available from Illumina and others) may be used to establish heterozygosity directly. So called "Next Generation Sequencing" platforms are particularly preferred.

Preferred embodiments of methods for determining aneuploidy of polar bodies and oocytes disclosed herein comprise the use of microarray systems. A microarray may include a population of different probe molecules that are attached to one or more substrates such that the different probe molecules can be differentiated from each other according to relative location. An array can include different probe molecules, or populations of the probe molecules, that are each located at a different addressable location on a substrate. Alternatively, a microarray can include separate optical substrates, such as beads, each bearing a different probe molecule, or population of the probe molecules, that can be identified according to the locations of the optical substrates on a surface to which the substrates are attached or according to the locations of the substrates in a liquid. Exemplary arrays in which separate substrates are located on a surface include, without limitation, a BeadChip Array available from Illumina®, Inc. (San Diego, Calif.), for example the GoldenGate BeadChip arrays and Infinium BeadChip arrays, or others including beads in wells such as those described in U.S. Pat. Nos. 6,266,459, 6,355,431, 6,770,441, 6,859,570, and 7,622,294; and PCT Publication No. WO 00/63437, each of which is hereby incorporated by reference. Other arrays having particles on a surface include those set forth in US 2005/0227252; WO 05/033681; and WO 04/024328, each of which is hereby incorporated by reference.

Any of a variety of microarrays known in the art, including, for example, those set forth herein, can be used. A typical microarray contains sites, sometimes referred to as features, each having a population of probes. The population of probes at each site is typically homogenous having a single species of probe, but in some embodiments the populations can each be heterogeneous. Sites or features of an array are typically discrete, being separated with spaces between each other. The size of the probe sites and/or spacing between the sites can vary such that arrays can be high density, medium density or lower density. High density arrays are characterized as having sites separated by less than about 15 µm. Medium density arrays have sites separated by about 15 to 30 µm, while low density arrays have sites separated by greater than 30 µm. An array useful in the invention can have sites that are separated by less than 100 µm, 50 µm, 10 µm, 5 µm, 1 µm, or 0.5 µm.

Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591, each of which is hereby incorporated by reference. A spotted microarray can also be used in a method according to an embodiment of the invention. An exemplary spotted microarray is a CodeLink™ Array available from Amersham Biosciences. Another microarray that is useful is one that is manufactured using inkjet printing methods such as SurePrint™ Technology available from Agilent Technologies.

The systems and methods set forth herein can be used to detect the presence of a defined SNP that may be present in a PB1, embryo, oocyte, or derivative thereof.

A preferred embodiment employs the Affymetrix GeneChip™ 10K Microarray which is designed to analyse 10,000 SNPs distributed at an average distance of 0.2 Kb across each of 22 chromosomes (see Matsuzaki, H. et al. Parallel genotyping of over 10,000 SNPs using a one-primer assay on a high-density oligonucleotide array. Genome Res. 14, 414-425 (2004) In the case of oligonucleotide chips, the oligonucleotides that can be bonded to a chip according to the invention will be capable of distinguishing biallelic SNPs across the genome. Preferred are 25 nucleotide-long oligonucleotides.

Thus in one embodiment the SNPs are interrogated on a "gene" or "oligonucleotide" chip or microarray. As is well known in the art these are miniaturized vehicles, in most cases made of glass or silicon, on whose surface oligonucleotides of known sequence are immobilized in an ordered grid of high density.

Another preferred embodiment employs the Illumina Infinium™ Human CytoSNP-12 Beadchip. This system enables genome-wide genotyping of about 300,000 SNP markers. The system is based on the random assembly of derivatized microscopic beads
 approximately 3 µm in size placed into wells of a patterned substrate, and permits specified combinations of SNPs to be interrogated. The Infinium microarrays were utilized in Examples of the disclosure, however any microarray platform appropriately designed could also be utilized.

Amplification

As used herein, "amplification" refers to any process for multiplying strands of nucleic acid, such as genomic DNA, in vitro.

Amplification techniques include, but are not limited to, polymerase chain reaction (PCR) library based methods; and isothermal amplification methods, such as Multiple Displacement Amplification (MDA). Such techniques are well known to those skilled in the art—see for example Ausubel et al., Short Protocols in Molecular Biology, (3rd ed.), Wiley & Sons; 2001, Sambrook and Russell, Molecular Cloning: A Laboratory Manual (3rd Edition); 1982, Maniatus et al., Molecular Cloning: A Laboratory Manual; DNA Cloning: A Practical Approach, vol. I & II (D. Glover, ed.); 1984; Spits, et al., 2006, Nature Protocols 1:1965-1970 "Whole genome multiple displacement amplification from single cells"; U.S. Pat. No. 6,124,120. Methods of whole genome amplification applicable to PGD are well known to those in the art and have been reviewed by Ying-ming Zheng, Ning Wang, Lei Li, and Fan in "Whole genome amplification in preimplantation genetic diagnosis" J Zhejiang Univ Sci B. 2011 January; 12(1): 1-11. doi: 10.1631/jzus.B1000196 PMCID: PMC3017410.

Systems

Preferably a system for use in the present invention would comprise means for SNP interrogation plus a programmed storage device or medium for causing a computer to analyse the resulting data. The SNP interrogation data could be stored for later analysis or analysed 'on the fly'—as used herein the term "database" covers both types of data source.

Preferred means for SNP interrogation would be an oligonucleotide chip which would interrogate at least the preferred chromosomes at the appropriate density in the vicinity of the centromere as discussed herein.

The methods disclosed herein may be implemented with the aid of a computer. Typically this would include a central processing unit (CPU) connected by a system bus or other connecting means to a communication interface, system memory (RAM), non-volatile memory (ROM), and one or more other storage devices such as a hard disk drive, a diskette drive, and a CD ROM drive.

The computer also includes a display device, such as a printer, CRT monitor or an LCD display, and an input device, such as a keyboard, mouse, pen, touch-screen, or voice activation system. The input device may receive data directly from the means for SNP interrogation via an interface (as for example with an Affymetrix or Illumina product based system).

The computer stores and executes various programs such as an operating system and application programs.

The computer-usable medium would cause the computer to analyse CH and assess the likelihood of aneuploidies of maternal origin in accordance with the methods described herein. The medium may for example be selected from the group consisting of a hard disk, a floppy disk, Random Access Memory, Read Only Memory and Electrically Erasable Programmable Read Only Memory.

Thus the invention provides a computer-usable medium having computer-readable program code or instructions stored thereon (i.e. a programmed storage device) for causing a computer to execute a method assessing the risk of chromosomal aneuploidy of maternal meiotic origin in a human egg following fertilisation, the method being any one of those discussed herein.

Preferably the method comprises:
(a) accessing a database comprising genotype data obtained from a plurality of consecutive SNP loci present in a chromosome of the PB1,
(b) determining a centromere position,
(c) determining the proportion of heterozygous SNPs in a region flanking the centromere position by determining the number of SNPs giving a heterozygosity call (n) compared to the total number of SNPs (t) in the region;
(d) determining that the corresponding fertilised egg or embryo is at higher risk of aneuploidy when the proportion exceeds a reference proportion.

Preferably the method comprises assessing the CH in a corresponding region of the chromosomes from a maternal (e.g. somatic) cell. Those SNPs which are non-heterozygous in the maternal data are uninformative, and the method may be based purely on, or weighted towards, those loci which are heterozygous in the maternal data.

The method may additionally or alternatively utilise assessing SNP loci present across a plurality of (preferably all) chromosomes of PB1 to detect unusually low levels of recombination, being indicative of a tendency to aneuploidy.

The method may additionally or alternatively utilise assessing SNP loci present across a plurality of (preferably all) chromosomes of PB1 to detect instances of single recombination events near the centromere or telomere.

The invention also provides a computer programmed to execute a method as described above.

It will be appreciated by those skilled in the art that the disclosed methods, to the extent to which it entails analysing SNPs in PB1 (optionally with PB2 also) to infer the nature of the maternal chromosomes in the fertilised egg or embryo, may be carried out in conjunction with other methodologies in which that data can also be utilised, or may be of interest, when determining aneuploidy or for diagnosing of other diseases or conditions in a subject. Examples include diagnosing disease by linkage, or diagnosing the presence or susceptibility to a disease or cancer associated with particular SNP alleles or haplotypes—for example known single gene defects relevant to disease risk (see e.g. Table I of WO2011/138750 of the MRC et al).

Definitions

Allele—Each normal somatic cell has two copies of the genome on pairs of homologous chromosomes. A single copy of a gene or DNA marker, which may differ in sequence from the other copy, is referred to as an allele. The term "allele" is used consistent with its meaning in the art of biology. An allele is one or more alternative forms of a gene, genetic sequence or single nucleotide (e.g. a single nucleotide polymorphism or SNP) found at a specific location, or locus, on a chromosome.

SNP—A single nucleotide polymorphism is a single base pair in the DNA sequence that varies between individuals. These occur frequently throughout the genome and are useful as markers. For example, biallelic SNPs can have either of two bases at a particular position which are referred to generically as 'A' and '13' herein.

Homologous chromosome—The human genome is duplicated in each cell on 23 pairs of homologous chromosomes, one of each pair inherited from the father and one from the mother.

Sister chromatid—DNA replication results in the duplication of each chromosome into two sister chromatids which remain tightly bound together until they separate and segregate to opposite poles during cell division.

Centromere—Specialised region of the chromosome which facilitates the attachment of spindle microtubules during cell division.

p arm—Term used for the shortest of the two arms of chromosomes with centromeres placed more or less centrally (also 'short arm').

q arm—Term used for the longest of the two arms of chromosomes with centromeres placed more or less centrally (also 'long arm').

Any sub-titles herein are included for convenience only, and are not to be construed as limiting the disclosure in any way.

The invention will now be further described with reference to the following non-limiting Figures and Examples. Other embodiments of the invention will occur to those skilled in the art.

The disclosure of all references cited herein, inasmuch as it may be used by those skilled in the art to carry out the invention, is hereby specifically incorporated herein by cross-reference.

FIGURES

FIG. 1—chromosome segregation in female meiosis I and II (1) Female meiosis is initiated in the fetal ovary before birth during the early development of the female germ cells (primary oocytes), which will eventually form mature eggs or oocytes in the adult female. (2) To reduce the number of chromosomes from the normal (euploid) 23 pairs of homologous chromosomes (one of each pair inherited from the father (left hand side, including representative allele A) and one from the mother (right hand side, including representative allele B), or 46 in total, to 23 single chromosomes, there is one round of DNA replication in which each chromosome is duplicated into two sister chromatids followed by two specialised meiotic divisions, meiosis I and II. The two sister chromatids have identical DNA sequences and therefore SNP genotypes at this stage, including the regions flanking the centromere as represented here in the boxes at the position of the centromeres, remain tightly bound together. (3) The two homologous chromosomes of each pair 'pair up' and a single bivalent chromosome forms in which all four sister chromatids are tightly bound together. This allows a limited number of breaks in the DNA strands of adjacent non-sister chromatids to 'crossover' and rejoin the other chromatid which results in the exchange of a chromosome segment from that point to the end of the chromosome arm. (4) As the cell divides at the end of meiosis I, one homologous chromosome of each pair is pulled into the first polar body (left) and the other into the secondary oocyte (right), which therefore now has 23 chromosomes each with two sister chromatids. Note also that the homologous chromosomes of paternal and maternal origin segregate at random according to Mendel's first law. In the diagram, a single crossover is illustrated between two non-sister chromatids.

When the two homologous chromosomes separate, therefore, there is one non-recombinant and one recombinant sister chromatid i.e. a chromatid which has exchanged part of the chromosome with the other homologous chromosome. Note that because crossovers generally occur some distance away from the centromere, at all maternal heterozygous positions flanking the centromere, the two sister chromatids of both homologous chromosomes are homozygous for one of the two maternal SNP alleles (copies). Beyond the position of the crossover towards the ends of the chromosome some SNP combinations on the two sister chromatids may be heterozygous. (5) In meiosis II, following fertilisation by a sperm cell containing the paternal half set of chromosomes, the two sister chromatids of each chromosome finally separate and segregate into the second polar body and fertilised oocyte or zygote. The zygote therefore inherits 23 single maternal chromatids (or more simply at this stage 'chromosomes').

Errors in this normal pattern of chromosome duplication and segregation during female meiosis can cause abnormal numbers of maternal chromosomes (aneuploidy) to be inherited in the zygote. Three basic mechanisms are known to be associated with these errors and are illustrated in FIGS. 2-4 and the euploid/aneuploid outcomes summarised in Table 1.

FIG. 2—female meiotic errors resulting in aneuploidy: (1) Classical non-disjunction of homologous chromosomes (Meiosis I) and sister chromatids (Meiosis II)

Normally the two homologous chromosomes, which make up the single bivalent chromosome, disjoin at the end of meiosis I, and move to opposite poles so that one homologous chromosome (with two sister chromatids) ends up in the first polar body (PB1; left) and the other in the secondary oocyte (right) (2.1). The classical textbook mechanism causing aneuploidy in human oocytes is the non-disjunction of either the two homologous chromosomes in meiosis I (2.4 and 2.5), or the two sister chromatids in meiosis II (2.2 and 2.3). Which homologous chromosome segregates to the secondary oocyte is random so there are two possible variants of 2.1-2.3. This mechanism is now known only to occur in a minority of cases of aneuploidy.

FIG. 3—female meiotic errors resulting in aneuploidy: (2) Premature predivision of sister chromatids (Meiosis I)

Premature predivision of sister chromatids is now considered to be the main mechanism causing aneuploidy in the human oocyte. This is where one of the two homologous chromosomes forming the single bivalent chromosome disjoins normally and is pulled to one or the other pole. However, the two sister chromatids of the other homologous chromosome separate prematurely and one sister chromatid segregates to the first polar body (PB1) (left) and one to the secondary oocyte (right). At meiosis II, the two sister chromatids of the intact homologous chromosomes (if present in the secondary oocyte) separate and segregate to the second polar body (PB2) and fertilised oocyte or zygote (as normal). The single sister chromatid segregates at random to either PB2 or the zygote. The zygote is therefore either euploid for that maternal chromosome (3.2 and 3.3) because the segregation of the single chromatid in meiosis II balanced the error in meiosis I, or is aneuploid (3.1 and 3.4). As the intact homologous chromosome randomly segregates either to PB1 or the secondary oocyte and similarly that either sister chromatid of the prematurely predividing homologous chromosomes can segregate to PB2 or zygote, there are 4 possible variants of 3.1-3.4

FIG. 4—female meiotic errors resulting in aneuploidy: (3) Biorientation of both homologous chromosomes (Meiosis I)

The third mechanism causing aneuploidy is where the two sister chromatids of both homologous chromosomes separate and segregate to opposite poles (biorient). In this case, two separate non-sister chromatids segregate to the first polar body (PB1; left) and the other two to the secondary oocyte (right). At meiosis II following fertilisation, both chromatids then segregate randomly to either pole and either one chromatid segregates to the second polar body (PB2) (right) and one to the fertilised oocyte or zygote (middle) (4.1) or both segregate together to either PB2 or zygote causing aneuploidy (4.2 and 4.3). Please note that because there are two possible combinations of non-sister chromatids in meiosis I and because of random segregation of chromatids in meiosis II, there are 4 variants of 4.1 and two each for 4.2 and 4.3.

FIG. 5—flow chart

This Figure shows a flow chart illustrating a process for aneuploidy prediction by centromeric heterozygosity analysis based on disclosed methods.

Figure 6:
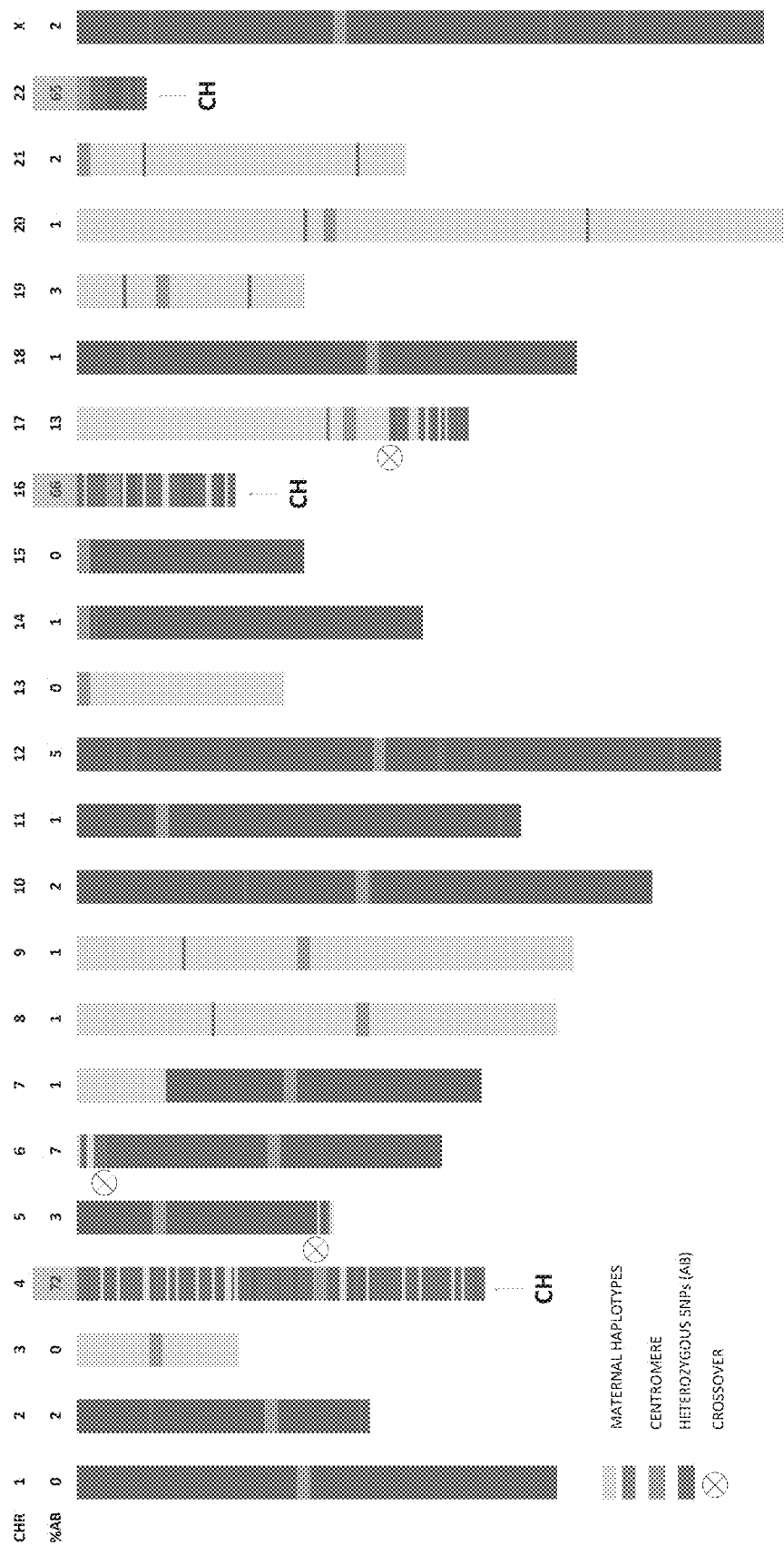

FIG. 6—centromeric heterozygosity detected in a first polar body (PB1)

For each autosome (1-22) and the X chromosome, the genotype of consecutive maternal heterozygous SNP loci flanking each centromere are represented by continuous columns in which the length is proportional to the number of loci. In the figure yellow [lighter] and green [darker] indicate homozygous SNP loci for the two maternal haplotypes and red represents heterozygous SNP loci. The position of the centromere for each chromosome is indicated by a light green band near the centre of the chromosome (or at the top of chromosomes 13-15 and 21-22).

Centromeric heterozygosity (CH) is present for chromosomes 4, 16 and 22 with 72, 66 and 65% heterozygous AB loci, respectively, interspersed with homozygous calls of either maternal haplotype caused by random allele dropout. Similar analysis of the corresponding metaphase II oocyte demonstrated that the CH for chromosomes 4 and 16 was caused by biorientation and segregation of sister chromatids in both homologous chromosomes since CH was also observed. Whereas for chromosome 22, maternal heterozygous loci close to the centromere were homozygous in the oocyte. This indicates that predivision of sister chromatids on one homologous chromosome had resulted in three chromatids segregating to PB1 and only a single chromatid to the oocyte which could have resulted in monosomy following fertilisation. All of the other chromosomes are homozygous in the region flanking the centromere for one of the two maternal haplotypes (yellow or green) demonstrating independent inheritance of one of the mothers' chromosomes (single homologue with two sister chromatids) (Mendel's first law) with only an occasional heterozygous miscall (these miscalls appear as one or more spaced-apart 'thin' lines on various of the chromosomes i.e. 2, 6-12, 14, 17-21, x).

Three crossovers are detected away from (distal to) the centromeres in chromosomes 5, 6, and 17. It should be noted that only the region flanking the centromere is shown so recombination is relatively infrequent. Beyond these crossovers a band of heterozygosity is present since one recombinant sister chromatid now has a segment from the other homologous chromosome. Again analysis of the corresponding metaphase II oocyte confirmed the presence of the other homologue (with two sister chromatids) with homozygous SNP loci for the opposite maternal haplotype and the same heterozygous banding pattern.

The apparent change from homozygosity from one haplotype to the other in chromosome 7 (green to yellow) is an artefact and results from a crossover in the reference genotype used to phase the A and B maternal alleles. This apparent complete step-change in the maternal haplotype can be readily detected and distinguished from the quite different pattern of calls resulting from true CH or crossover distal to the centromere, and can thus be ignored in the analysis.

Figure 7:
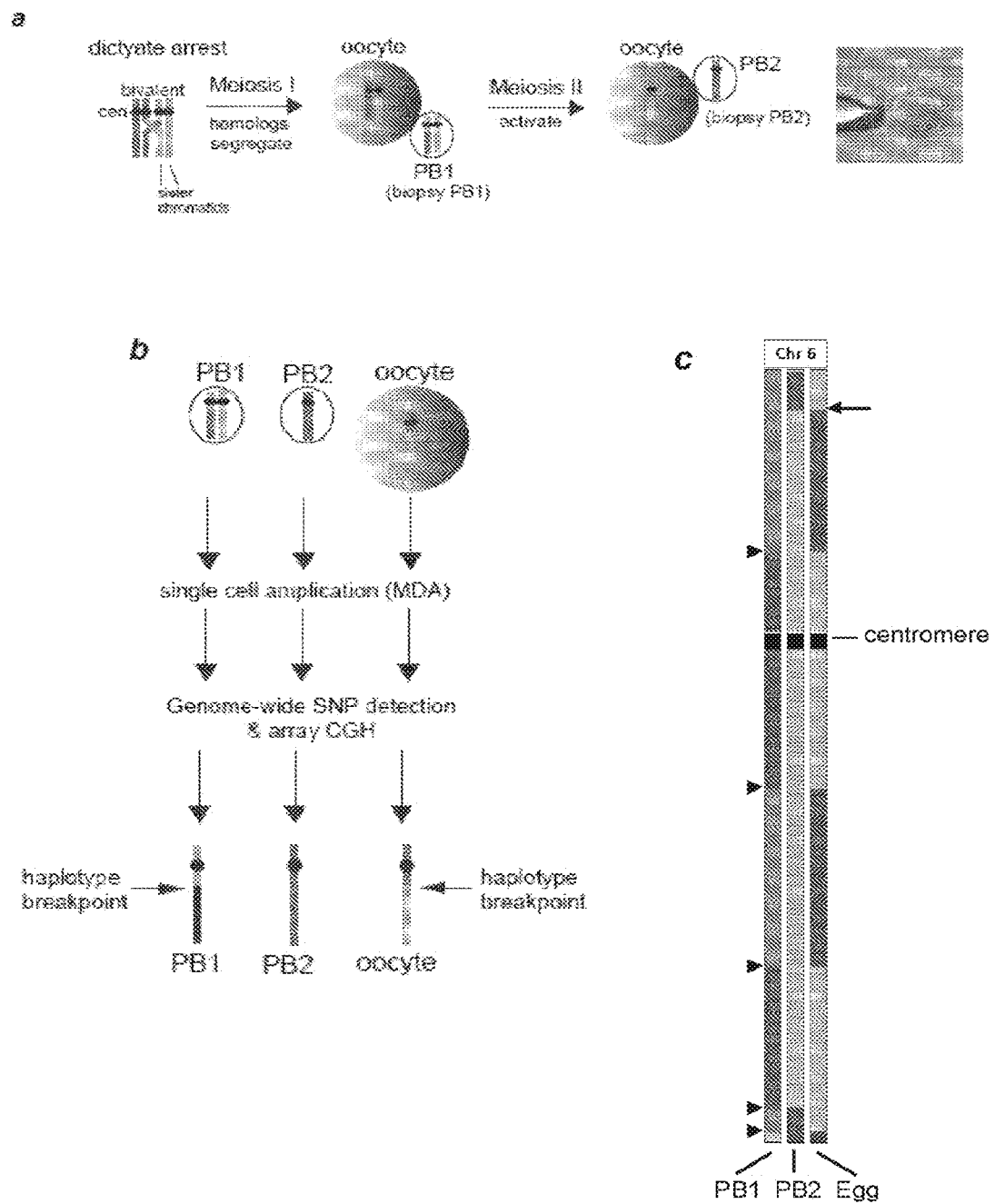

FIG. 7—Mapping recombination in all three products of meiosis in adult human oocytes (a) Crossing over and bivalent formation between homologous chromosomes during foetal development. Upon oocyte maturation, homologous chromosomes (defined by pericentromeric genetic markers) segregate and PB1 is formed. These mature MII oocytes arrest again, before being activated by sperm (or Ca2+ ionophore) and completing the second meiotic division. To the right, a brightfield image of an activated oocyte with PB2 is shown.

(b) Schematic of MDA amplification of DNA from PB1, PB2 and oocyte in three separate reactions followed by hybridization to the Illumina 300K SNP array. The readout from the SNP array is shown at the bottom. The haplotype breakpoint can be seen in the oocyte and a reciprocal heterozygous block is present in the PB1. Note that the SNPs in this region of PB1 cannot be phased.

(c) Schematic of chromosome showing crossovers, which can be ascertained by heterozygosity analysis of PB1 (arrowheads, left hand side) and those requiring PB2 or oocyte analysis (arrow, right hand side).

Figure 8:
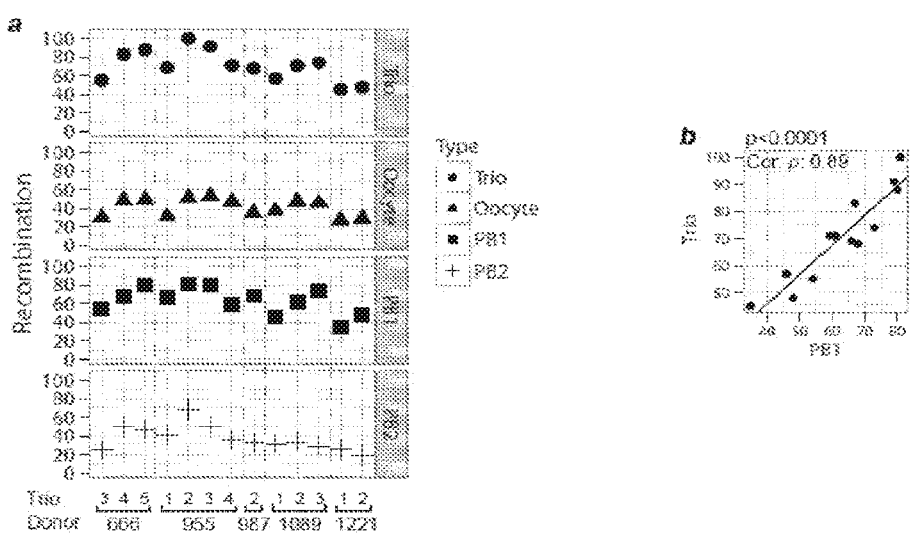

FIG. 8—Crossover distribution and crossover tract lengths in human female meiosis.

(a) Recombination events estimated from the oocyte-PB trios (Trio), oocyte only, PB1 only and PB2 only in one to four oocytes from five different donors.

(b-e) Spearman correlation (p) between crossover levels based on Trio and PB1, Trio and oocyte, trio and PB2 and oocyte and PB2. Note that Wilcox tests gave significant values, but not for (e).

FIG. 9—Histogram summarising results of Table 2 in Example 3

The histogram clearly demonstrates the relationship between the PB1 heterozygosity pattern and embryo karyotype.

EXAMPLES

Example 1—Meiotic Errors that can Lead to Aneuploidy in a Fertilized Egg

As illustrated in FIG. 1, normally in meiosis I the two homologues of each chromosome, now consisting of pairs of sister chromatids, pair up and join together, homologous non-sister chromatids undergo one or more recombinations or crossovers.

Subsequently the homologous chromosomes of the condensed bivalent chromosome are 'co-oriented' to the same spindle poles, so that the homologous chromosomes separate away from each other into PB1 and the secondary oocyte. In meiosis II, the two sister chromatids separate into PB2 and fertilised oocyte (zygote or egg) following fertilisation.

It can thus be seen that in the in the normal (euploid) oocyte all centromeric regions of each chromosome are homozygous in PB1, since this part of the sister chromatids will generally not be significantly affected by recombination or crossovers.

The primary oocyte in the fetal ovary has 23 pairs of homologous chromosomes (46 in total), one inherited from the father and one from the mother, as in somatic cells.

1001—Representative maternal heterozygous (AB) SNP close to centromere.
1002—Pair of homologous chromosomes (blue and red)
1003—Primary oocyte Following DNA replication early in meiosis I both homologous chromosomes consist of pairs of sister chromatids closely bound together, with identical duplicated SNPs.

1004—Short or 'p' arm
1005—Position of centromere
1006—Long or 'q' arm
1007—Pair of sister chromatids Homologous chromosomes pair and all four sister chromatids are closely bound together into 23 thread-like bivalent chromosomes. The chromatids break and non-sister chromatids join up and exchange parts of chromosome arms at crossovers.

1008—Single bivalent chromosome (shown diagrammatically in 2D
1009—Single crossover on the long arm between two non-sister chromatids Prior to ovulation in the adult, the maturing oocyte completes meiosis I. The two homologous chromosomes within each bivalent segregate into the first polar body (PB1) and secondary oocyte which arrests in metaphase of meiosis II.

1010—First polar body (PB1)
1011—Secondary oocyte
1012—Exchanged chromosome segments from the position of the crossover to the end of the chromosome arm At fertilization, meiosis II is completed and the two sister chromatids in the secondary oocyte segregate into the second polar body (PB2) and fertilized oocyte or zygote reducing maternal chromosome number from 46 to 23 (paternal chromosomes not shown).

1013—Single chromatids (or simply chromosomes)
1014—Second polar body (PB2)
1015—Fertilised oocyte or zygote As illustrated in FIG. 2, a classical textbook mechanism causing errors in meiosis is 'non-disjunction' of homologous chromosomes in meiosis I and sister chromatids in meiosis II.

Where this kind of error has occurred, analysis of CH or loss of centromeric DNA in PB1, would detect these errors in meiosis I. This type of error is now known to be rare.

As illustrated in FIG. 3, another source of errors is 'premature predivision of sister chromatids' in meiosis I. Copy number analysis by array CGH has confirmed this is the predominant mechanism causing aneuploidy in advanced maternal age (Handyside et al., 2012). Gain of a sister chromatid would be detected by CH in PB1 but loss of a sister chromatid would not be detected as the centromere would appear to be homozygous.

All of the above errors in meiosis I can be detected by quantitation using prior art methods such as 24Sure™ (BlueGnome, Cambridge UK) following manufacturer's protocol.

As illustrated in FIG. 4, it has also been determined that errors may arise in meiosis I whereby both homologous chromosomes 'bi-orient' sister chromatids to opposite spindle poles and separate at meiosis I, in a 'mitosis-like' division. The two unpaired sister chromatids then are likely to segregate randomly to either pole at meiosis II and in 50% of cases, both sister chromatids will either segregate to PB2 or the oocyte resulting in aneuploidy. Furthermore it has been shown that this increased risk of aneuploidy in the resulting fertilised egg following meiosis II, arising from the original separation of sister chromatids in meiosis I, can be detected by CH in PB1.

In particular normal euploid oocytes would be expected to have all centromeric heterozygous loci homozygous in PB1, whereas one or more centromeres heterozygous or missing in PB1 would imply an at-risk oocyte.

In will be understood that combining detection of CH in PB1 with quantitation would be fully informative for meiosis I errors (see FIGS. 1(3)) while also being able to assess risk of meiosis II errors even where there is an apparently normal (euploid) PB1.

Example 2—Assessment of CH in PB1 from Number of Different Oocytes

In this example the status of defined SNPs were assessed in PBs ("PB1 genotype") and corresponding secondary oocytes ("Egg genotype").

Methods

PBs and oocytes were lysed and the whole genome amplified (WGA) by multiple displacement amplification according to manufacturer's instructions (Repli-g, Qiagen). WGA products were then genotyped on a SNP genotyping bead array again according to the manufacturer's protocol (Infinium Human CytoSNP-12, Illumina). The genotype data was exported as a text file and imported into Microsoft Excel and a macro was used to identify SNPs flanking the centromeres of each chromosome and display the results. The macro also calculated the percentage of heterozygous SNPs.

The maternal genotype was ascertained using the same bead array but genomic DNA isolated from a blood sample by standard methods was used. This data was also imported into Excel and used to identify all of the heterozygous SNPs in the regions of the centromeres so that the subsequent analysis of the PB1s could be limited to only these loci.

Using this method 200 SNPs flanking each of the centromeres of the 18 non-acrocentric chromosomes and on the q arm of the 5 acrocentric chromosomes for a total of 8200 defined SNPs (18×400+5×200) were assessed in PBs and secondary oocytes.

Theoretical Considerations

Theoretically, the abnormal presence of two non-sister chromatids, one each from the two homologous chromosomes, should result in all heterozygous maternal SNP loci flanking the centromere to the position of the first crossover also being heterozygous in PB1. Analysing only maternal heterozygous loci (as shown in FIG. 6) would therefore result in a continuous series of heterozygous SNPs to the point of the crossover, when all of the SNPs would be homozygous.

These homozygous SNPs beyond the cross over, will be consistent with one or the other of the maternal haplotypes (if the maternal SNPs are phased).

In practice, when genotyping single cells following whole genome amplification, failure to amplify one of the two SNP copies at each heterozygous locus (allele dropout or ADO) is relatively frequent (up to approximately 50%). Therefore the expected pattern in PB1 for the abnormal situation is a chromosome with a high incidence of heterozygous loci, including around the centromere (CH), but interspersed with homozygous SNPs of either maternal haplotype at random.

Beyond the crossover there may still be the occasional genotyping error ('miscalls' or 'drop-ins') resulting in a homozygous SNP to be called as heterozygous (approximately 5-10%).

Results

The results are shown in FIG. 6 for one egg (termed 'Egg9'). Data showed there were relatively low levels (<=5%) of AB 'miscalls' or 'drop-ins' for most chromosomes (i.e. a low incidence of where the mother was determined not to be heterozygous, but the PB1 associated with Egg9 was called as heterozygous).

A high level of centromeric heterozygosity (CH) for chromosomes 4, 16 and 22 was found when evaluating PB1 associated with Egg9

The three affected chromosomes (4, 16 and 22) demonstrate the theoretical pattern explained above, with a high incidence of heterozygous loci close to the centromere interspersed with homozygous SNPs of either maternal haplotype at random due to ADO.

As can be readily seen in FIG. 6, the presence of this ADO did not prevent the accurate detection of CH.

Similar analysis of the corresponding metaphase II oocyte (not shown) demonstrated that two of these (4 and 16) were caused by biorientation of both homologues so that the centromeres in the oocyte were also heterozygous. For chromosome 22 the CH was caused by premature predivision of sister chromatids with an extra chromatid being inherited in PB1 and the oocyte chromosome was homozygous in the region of the centromere. The former would therefore have normal copy number and the aneuploidy risk would not be detected by array CGH.

Additionally, chromosome 17 had elevated heterozygous levels, but this was found to be due to a crossover close to the centromere on the q arm, which resulted in distal heterozygosity (i.e. away from the centromere) which could be readily distinguished from the affected chromosomes.

Prognostic Use

Due to presence of a high level of CH in the PB1 associated with Egg9, Egg9 can be classified as higher risk than a corresponding Egg in which CH was lower in its associated PB1 or absent.

In conclusion, chromosomes 4 and 16 demonstrated high CH in both products of meiosis I (PB1 and secondary oocyte) of Egg9. Both homologues of these chromosomes have divided in a 'mitosis-like' way resulting in one chromatid for each homologue in both PB1 and meiosis II oocyte. It is notable that as the copy number of these chromosomes is normal in PB1 (2n chromatids) this is not detected by array CGH. However, as there is no DNA replication in meiosis II, the two single chromatids will theoretically segregate at random resulting in a 50% risk of aneuploidy in the fertilised oocyte (FIG. 4).

With chromosome 22, there is a high level of CH in PB1 but not the secondary oocyte. This indicates chromatid gain in PB1 and a 50% risk of loss in the fertilised oocyte (cf. FIG. 1(3)). In absence of data from the secondary oocyte, this could be confirmed by quantitative analysis of PB1.

The cumulative binomial probability that at least one of these chromosomes will result in aneuploidy is therefore 0.875.

Thus it can be seen that assessing the presence or degree of centromeric heterozygosity in chromosomes of the first polar body of the egg can be used to assess the risk of chromosomal aneuploidy of maternal meiotic origin.

Example 3—Comparison of Array CGH for Quantitative Detection of Aneuploidy in PB1 and PB2 with SNP Genotyping, Maternal Haplotyping and Total Heterozygosity and/or CH Analysis in PB1 Alone, or PB1 and PB2

Ten mature MII arrested oocytes were collected from a patient having aneuploidy testing by array CGH of PB1 and PB2. PB1 was biopsied from each oocyte prior to intracytoplasmic sperm microinjection and, following fertilisation and resumption of meiosis, PB2 was also biopsied. Both polar bodies were lysed, DNA amplified by WGA and aliquots of the products used for array CGH. The array CGH results indicated that all of the embryos had one or more copy number abnormalities in PB1 and/or PB2 except one, presumed euploid embryo (Embryo #1), which was therefore selected for transfer (Table 2). With the patients consent, the remaining 9 presumed aneuploid embryos were lysed and the DNA amplified by WGA. Genomic DNA from both parents, WGA products from all polar bodies and the corresponding embryos were then SNP genotyped. A combination of (1) maternal haplotyping using a PB2 as a reference to phase the heterozygous maternal SNPs, (2) heterozygosity analysis, and (3) haplotyping of both parental chromosomes in the embryo (Handyside et al, 2010) was then used to analyse the pattern of crossovers genome wide in PB1, PB2 and the corresponding embryos.

SNP analysis of the PBs and the corresponding embryos were 100% concordant and confirmed that 7/9 embryos predicted to be aneuploid by array CGH of PB1 and PB2, were aneuploid. However, the remaining two embryos (Embryos #2 and 12; Table 2) with three and multiple copy number abnormalities, respectively, identified by array CGH were euploid (Table 2; see also FIG. 9). Furthermore, no abnormal SNP patterns, including total and/or centromeric heterozygosity, were detected for any of the chromosomes in these two euploid embryos. In contrast, 19 examples of abnormal SNP patterns occurred in the 7 aneuploid embryos (bold indicates an aneuploid outcome in the corresponding embryo):

1× MI NDJ (see FIGS. 2.4, 2.5)
3× PD (1× balanced (see FIG. 3.2), 2× unbalanced (FIG. 3.4))
15× BO (11× balanced, 4× unbalanced; see FIGS. 4.1 vs. 4.2, 4.3)

The 11× balanced BO were all confirmed as having opposite centromeric haplotypes in PB2 and embryo (FIG. 4.1).

Therefore, whereas array CGH analysis of PB1 alone would have predicted the possibility of 3/7 aneuploidies, analysis of the distribution of heterozygous SNPs in PB1 alone included abnormalities for 7/7 of the aneuploid chromosomes plus 12 other abnormalities associated with increased risk of aneuploidy. This demonstrates the utility of using PB1 heterozygosity assessment for diagnostic or prognostic screening.

More specifically 7/7 aneuploidies were predicted based on analysis of haplotypes in:
9× cen het (embryo 7, 8, 10, 11, 13, 14, 16)->1× MI trisomy
1× monosomy
7× hetero (embryo 8, 10, 13, 14)->2× monosomy 2× homo (embryo 7, 10)->2× MI trisomy
1× loss (embryo 11)->1× MI trisomy

TABLE 2

Example data comparing array CGH analysis of chromosome copy number in PB1 and PB2 with SNP genotyping and maternal haplotyping, and parental haplotyping (karyomapping) of the corresponding embryos.

| Embryo # | Array CGH | | Mat haplotyping | | Type of abnormality | Karyomapping of embryo |
|---|---|---|---|---|---|---|
| | PB1 | PB2 | PB1 | PB2 | | |
| 1 | Euploid | Euploid | Euploid | Euploid | None | Transferred |
| 2 | +6, +10, +18 | Euploid | Euploid | Euploid | None | Euploid |
| 7 | -22 | Euploid | 16-cen het 21-cen het 22-homo | Euploid | 16-BO bal 21-BO bal 22-PD unbal | +22 MI |
| 8 | +15 | -9, -15 | 9-cen het 15-hetero | -9, -15 | 9-BO unbal 15-PD bal | +9 MI |
| 10 | -15, -19, -22 | Euploid | 15-homo 16-hetero 19-hetero 21-cen het 22-cen het | Euploid | 15-PD unbal 16-BO bal 19-BO bal 21-BO bal 22-BO bal | +15 MI |
| 11 | -22 | +22 | 4-cen het -22 | 22-cen het | 4-BO bal 22-MI NDJ | +22 MI |
| 12 | Euploid | Multiple copy number abnormalities | Euploid | Euploid | None | Euploid |
| 13 | Euploid | del 4, +22 | 16-cen het 21-hetero 22-hetero | del 4 22-hetero | 16-BO bal 21-BO bal 22-BO unbal | -22 MI |
| 14 | Euploid | -10, -13, +19, -20 | 17-cen het 19-hetero 22-hetero | 19-hetero | 17-BO bal 19-BO unbal 22-BO bal | -19 MI |
| 16 | Euploid | +21 | 21-cen het | 21-cen het | 21-BO unbal | -21 MI |

NDJ = Non-disjunction (see FIG. 2);
PD = Premature Predivision (see FIG. 3);
BO = Biorientation (see FIG. 4);
Euploid (a normal number of maternal chromosomes);
Del = partial deletion;
Bal = balanced;
Unbal = unbalanced;
NR = No results!

Example 4—Meiotic Recombination Analysis

It is known in the art that a low incidence and/or abnormal pattern of recombination close to the centromere or telomere is associated with abnormalities in chromosome segregation leading to aneuploidy (see Hassold, 2001). For example in the human population, the US National Down Syndrome project have reported that the rate of chromosomes 21 lacking recombination events is enriched in patients with Trisomy 21 compared to healthy individuals.

A similar analysis to that described above for Example 3, was carried out with 13 oocytes from 5 patients. However, in this example, following biopsy of PB1, resumption of MII and extrusion of PB2 was initiated by artificially activating the oocytes (FIG. 7a). Both polar bodies and the activated oocyte were then lysed, DNA amplified by WGA and SNP genotyped together with genomic DNA from the patient (FIG. 7b). Using the genotype of one of the PB2s or eggs, the two maternal haploptyes were then ascertained and analysed along with the pattern of heterozygosity in PB1, PB2 and the corresponding activated oocytes. This enabled genome-wide maps of meiotic recombination by analysis of the maternal haplotypes present.

Crossovers (recombination) between the homologous chromosomes (i.e. between two non-sister chromatids) results in a switch in haplotype distal to the haplotype breakpoint in both PB1 and either the PB2 or egg, but not both (FIG. 7c, arrowheads). In PB1, which normally retains both sister chromatids for one homologue, this results in heterozygosity distal to the first breakpoint (blue) followed by alternating bands of homozygosity and heterozygosity at successive crossovers towards the telomere of each chromosome arm. Whereas in PB2 or egg, which normally has only a single chromatid from the other homologue, this results in a switch from one haplotype to the other (yellow to green or vice versa) and the entire chromosome is homozygous. Thus, the number and position of these crossovers can be ascertained by analysing the number and position of regions of heterozygosity in PB1 alone. In addition, however, crossovers can also occur between sister chromatids in regions where a proximal crossover resulted in sister chromatids with opposite haplotypes. These can only be detected by examining the pattern of haplotype switching in PB2 and/or oocyte (FIG. 7c, arrow) since they only involve one of the two homologous chromosomes. In the corresponding heterozygous regions of the other homologous chromosome in PB1, these crossovers cannot be detected at all by genotype analysis, since both sister chromatids (with opposite haplotypes) switch haplotypes and the chromosome remains heterozygous. Thus the closest estimate of the position and total number of crossovers for each chromosome is the sum of those which can be detected by PB1 analysis alone and those occurring only in PB2 and oocyte.

Analysis of the pattern of heterozygosity and maternal haplotypes in the 13 activated oocytes revealed 920 crossovers in the 23 chromosomes analysed (22 autosomes and the X chromosome). There was a wide variation in the overall number of crossovers detected in PB1, PB2 and oocyte and total number (trio) in individual oocytes (FIG. 8a).

However, the number of crossovers in PB1 was highly correlated with the total number combining analysis of PB1, PB2 and oocyte ('Trio') (FIG. 8b).

Thus the number of crossovers in PB1, which is determinable using the methods described herein can be used as a tool or additional tool for assessing risk of aneuploidy in the oocyte. That in turn can be used in oocyte or embryo selection and/or as a prognostic indicator of likelihood of pregnancy.

Example 5—High Resolution SNP Mapping of PB1 can Reveal De Novo Structural Chromosome Abnormalities In humans, chromosomal abnormalities either in structure or numbers contribute towards disorders, infertility, and pregnancy loss (Nagaoka, 2012).

The analysis by the inventors of all products of meiosis described in Examples 3 and 4 above, allowed them to discern de novo alterations to chromosomes that could be specifically assigned to the human female germline.

For example in the data described in Example 4, three major structural defects (0.5% of chromosomes) from three different oocytes, were observed, all of which included imbalance in the oocyte itself.

One consisted of the gain of small piece of the q-arm of chromosome 22 (1.5 Mb) concomitant with the loss of the majority of the q-arm in the oocyte. Both the gain and loss was reflected in the PB1. The loss effectively leads to an aneuploid oocyte and would be predicted to cause embryo loss. In human, even a relatively small deletion of 22q13.3 is associated with Phelan-McDermid syndrome (Phelan, 1993).

The second structural change was the addition of 9.2 Mb of the p-arm of chromosome 8 in the oocyte, with concomitant loss in the PB1. This could either be an inversion—duplication or a non-chromosomally associated fragment of chromosome 8. Gain of 8p is associated with myeloproliferative syndrome (Macdonald, 1995).

Finally, nearly 2/3 of the q-arm of chromosome 15 was present twice in a third oocyte, with a concomitant loss in the PB1.

These observations support the conclusion that the structural defects arose during meiosis in female germline, and that PB1 can be used to observe or infer the possible presence of such defects.

REFERENCE LIST

Chowdhury, R., Bois, P. R., Feingold, E., Sherman, S. L. & Cheung, V. G. Genetic analysis of variation in human meiotic recombination. PLoS Genet 5, e1000648, doi: 10.1371/journal.pgen.1000648 (2009).

Handyside A H, Harton G L, Mariani B, Thornhill A R, Affara N, Shaw M A, Griffin D K (2009) "Karyomapping: a universal method for genome wide analysis of genetic disease based on mapping crossovers between parental haplotypes" J Med Genet. 2010 October; 47(10):651-8.

Handyside, A. H., Montag, M., Magli, M. C., Repping, S., Harper, J., Schmutzler, A., Vesela, K., Gianaroli, L., and Geraedts, J. (2012). Multiple meiotic errors caused by predivision of chromatids in women of advanced maternal age undergoing in vitro fertilisation. Eur J Hum Genet 70, 742-7

Hassold, T. and Hunt, P. (2001). To err (meiotically) is human: the genesis of human aneuploidy. Nat Rev Genet 2, 280-91.

Kong, A. et al. Sequence variants in the RNF212 gene associate with genome-wide recombination rate. Science 319, 1398-1401, doi:10.1126/science.1152422 (2008).

Macdonald, D., Aguiar, R. C., Mason, P. J., Goldman, J. M. & Cross, N. C. A new myeloproliferative disorder associated with chromosomal translocations involving 8p11: a review. Leukemia 9, 1628-1630 (1995).

Nagaoka, S. I., Hassold, T. J. & Hunt, P. A. Human aneuploidy: mechanisms and new insights into an age-old problem. Nat Rev Genet 13, 493-504, doi:10.1038/nrg3245 (2012).

Phelan, K. & Rogers, C. in GeneReviews (eds R. A. Pagon et al.) (1993).

Spandorfer, S. D., Davis, O. K., Barmat, L. I., Chung, P. H., and Rosenwaks, Z. (2004). Relationship between maternal age and aneuploidy in in vitro fertilization pregnancy loss. Fertil Steril 81, 1265-9.

The invention claimed is:

1. A system for selecting a human egg for transfer in an in vitro fertility procedure, the human egg comprising a first polar body (PB1), the first polar body comprising one or more PB1 chromosomes, the system comprising:
   an oligonucleotide microarray configured to perform a nucleic acid detection assay to interrogate genotype data of at least 25 biallelic SNPs flanking the centromeres of said one or more PB1 chromosomes, said SNPs in a region located within 5 to 10 Mb of the centromere, and
   a computer readable medium having stored thereon non-transitory computer-readable instructions for:
   a) accessing a database comprising genotype data obtained from said microarray,
   b) quantifying said biallelic SNPs that are heterozygous relative to a total number of SNPs in the region, to obtain a proportion of heterozygous SNPs,
   c) comparing the proportion of heterozygous SNPs to one or more threshold values associated with high levels of centromeric heterozygosity; and
   d) classifying the one or more PB1 chromosomes as having (i) a high degree of centromeric heterozyosity (CH) or (ii) a low degree of centromeric heterozygosity, based on the comparison of the proportion of heterozygous SNPs to the one or more threshold values; and
   e) outputting, to a display device. instructions to selectively transfer said human egg ahead of other eggs when said human egg is classified as having a low degree of centromeric heterozygosity.

2. The system of claim 1, further comprising instructions for determining the risk that the human egg will give rise to an aneuploid fertilised egg or embryo following meiosis II, wherein the presence or a higher level of CR in the first polar body indicates a higher risk of said chromosomal aneuploidy in the corresponding fertilised egg or embryo developed therefrom compared to where an absence or lower level of CH is present in the first polar body.

3. The system of claim 1, further comprising instructions for
   assessing the total number of crossovers in the PB1 chromosomes, based on the heterozygosity of some or all of the chromosomes of the first polar body of the egg, and
   determining the risk that the human egg will give rise to an aneuploid fertilised egg or embryo, wherein a below average total number of crossovers determined in the PB1 chromosomes indicates a higher risk of aneuploidy, compared to where an average number of crossovers is determined in the PB1 chromosomes.

4. The system of claim 1 further comprising instructions for
   assessing the position of crossovers in said one or more of the PB1 chromosomes, based on the heterozygosity of one or more of the chromosomes of the first polar body of the egg, and
   determining the risk that the human egg will give rise to an aneuploid fertilised egg or embryo, wherein a PB1 chromosome having only a single crossover proximal to the telomere or centromere indicates a higher risk of aneuploidy, compared to a PB1 chromosome having a plurality of medially distributed crossovers.

5. The system of claim 1 further comprising instructions for
   assessing the presence of structural defects in said one or more of the PB1 chromosomes, based on the heterozygosity of one or more of the chromosomes of the first polar body of the egg, and
   determining the risk that the human egg will give rise to an aneuploid fertilised egg or embryo, wherein a PB1 chromosome showing a structural defect indicates a higher risk of aneuploidy.

6. The system of claim 5 wherein the structural defects are chromosomal or sub-chromosomal defects selected from: gains, losses, and duplications.

7. The system of claim 1 further comprising instructions for
   distinguishing (i) a polar body which contains a chromosome consisting of sister chromatids replicated from one of the homologous chromosomes from the mother, from (ii) a polar body wherein the chromosomes comprise two or more non-sister chromatids being collectively derived from both of the homologous maternal chromosomes, and
   determining the risk that the human egg will give rise to an aneuploid fertilised egg or embryo, wherein (ii) indicates a higher risk of chromosomal aneuploidy of maternal meiotic origin in the corresponding egg.

8. The system of claim 1 further comprising instructions for assessing a plurality of different first polar bodies such as to grade the corresponding eggs, or fertilised eggs or embryos developed therefrom, according to their risk of possible chromosomal aneuploidy of maternal meiotic origin.

9. The system of claim 1 wherein the polar body is from a human female who has previously been diagnosed as having fertility problems or having or carrying an inheritable disease.

10. The system of claim 1 wherein the polar body is from a human female who is undergoing IVF treatment.

11. The system of claim 9 further comprising instructions for
    determining the risk of possible chromosomal aneuploidy of maternal meiotic origin, and
    based on said risk of possible chromosomal aneuploidy, determining a likelihood of pregnancy in said human female.

12. The system of claim 1 wherein the instructions include instructions for assessing at least 5, 10, 15 or 20 chromosomes per polar body.

13. The system of claim 1 wherein the instructions include instructions for assessing centromeric heterozygosity for 2 or more of the human chromosomes selected from the group consisting of: X, 22, 21, 18, 16 and 13.

14. The system of claim 1 further comprising a means for whole genome amplification of said first polar body prior to said nucleic acid detection assay.

15. The system of claim 1 wherein said instructions for classifying the one or more PB1 chromosomes further comprise instructions for:
  phasing the SNPs of the maternal chromosomes; and
  (ii) based on the SNP phasing from step (i), determining the presence of centromeric heterozygosity (CH) from any biallelic SNPs which are heterozygous maternal loci, but wherein said nucleic acid detection assay gives a homozygous call due to random allele dropout.

16. The system of claim 1 wherein the genotype data is obtained from at least 30, 40, 50, 75, 100, 200, 300, 400, 500 or more SNPs flanking the centromere, and wherein the genotype data is obtained from SNPs on both of the p and q arms of non-acrocentric chromosomes.

17. The system of claim 1, further comprising instructions for comparing the proportion of heterozygous SNPs in the first polar body to a proportion of heterozygous SNPs in a maternal cell genotype, wherein the maternal cell genotype comprises at least 10, 15, 20, 25, 50, 100 or more heterozygous SNPs.

18. A system for selecting a human egg for transfer in an in vitro fertility procedure, the human comprising a first polar body (PB1), the first polar body comprising one or more PB1 chromosomes, the system comprising:

a next generation sequencing platform configured to interrogate genotype data of at least 25 biallelic SNPs flanking the centromeres of said one or more PB1 chromosomes, said SNPs in a region located within 5 to 10 Mb of the centromere, and a computer readable medium having stored thereon non-transitory computer-readable instructions for:
a) accessing a database comprising genotype data obtained from said sequencing platform;
b) quantifying said biallelic SINN that are heterozygous relative to a total number of SNPs in the region, to obtain a proportion of heterozygous SNPs,
c) comparing the proportion of heterozygous SNPs to one or more threshold values associated with high levels of centromeric heterozygosity; and
d) classifying the one or more PB1 chromosomes as having (i) a high degree of centromeric heterozyosity (CH) or (ii) a low degree of centromeric heterozygosity, based on the comparison of the proportion of heterozygous SNPs to the one or more threshold values; and
e) outputting, to a display device, instructions to selectively transfer said human egg ahead of other eggs when said human egg is classified as having a low degree of centromeric heterozygosity.

* * * * *